United States Patent [19]
Oftring et al.

[11] Patent Number: 6,004,923
[45] Date of Patent: Dec. 21, 1999

[54] FATTY ACID DERIVATIVES AND THEIR USE AS SURFACTANTS IN DETERGENTS AND CLEANERS

[75] Inventors: Alfred Oftring, Bad Dürkheim; Martin aus dem Kahmen, Ludwigshafen; Christian Ott, Speyer; Günter Oetter, Frankenthal; Richard Baur, Mutterstadt, all of Germany

[73] Assignee: BASF Aktiengesellschaft, Ludwigshafen, Germany

[21] Appl. No.: 09/051,915

[22] PCT Filed: Oct. 21, 1996

[86] PCT No.: PCT/EP96/04560

§ 371 Date: Apr. 27, 1998

§ 102(e) Date: Apr. 27, 1998

[87] PCT Pub. No.: WO97/16408

PCT Pub. Date: May 9, 1997

[30] Foreign Application Priority Data

Oct. 27, 1995 [DE] Germany .............................. 195 40 091
Feb. 29, 1996 [DE] Germany .............................. 196 07 642
May 22, 1996 [DE] Germany .............................. 196 20 613

[51] Int. Cl.$^6$ ........................................................ C11D 3/30
[52] U.S. Cl. ........................... 510/499; 510/470; 510/488; 510/490

[58] Field of Search ...................................... 510/488, 502, 510/480, 470, 499

[56] References Cited

U.S. PATENT DOCUMENTS 5,488,139  1/1996  Dragner et al. .......................... 560/155
5,576,416  11/1996  Walker ...................... 528/340

FOREIGN PATENT DOCUMENTS

336267 A2  10/1989  European Pat. Off. .
2734596  2/1979  Germany .
4238211  1/1994  Germany .

OTHER PUBLICATIONS

"Tide" box. 1950 No Month Available.

*Primary Examiner*—Yogendra Gupta
*Assistant Examiner*—John R. Hardee
*Attorney, Agent, or Firm*—Oblon, Spivak, McClelland, Maier & Neustadt, P.C.

[57] ABSTRACT

Fatty acid derivatives based on epoxidized unsaturated fatty acid esters or triglycerides and reacted with amines such as hydroxy- and/or amino-substituted hydrophilic amines or amino acids and/or with alkanols or with water on the epoxy group and/or the carboxylic ester groups are described. These fatty amides are suitable as surfactants in detergents and cleaners.

9 Claims, No Drawings

FATTY ACID DERIVATIVES AND THEIR USE AS SURFACTANTS IN DETERGENTS AND CLEANERS

The present invention relates to the use of fatty acid derivatives of the general formula I

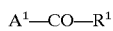

$$A^1\text{—}CO\text{—}R^1 \qquad \qquad I$$

as surfactants for cleaner systems for cleaning grease-soiled nontextile material, where the substituents have the following meanings:

$A^1$ an aliphatic $C_8$–$C_{24}$ radical with unbranched carbon chain, which contains in the chain one or more groups of the formula II

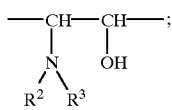

$R^1$ an —$N(R^2)R^3$ radical, a hydroxyl radical and its alkali metal or ammonium salts, a $C_1$–$C_4$-alkoxy radical or a radical of a mono-, di- or triglyceride, it being possible for the two latter to be radicals of natural saturated or unsaturated fatty acids or identical or different radicals $A^1$;

$R^2$ a hydrophilic radical having 2–40 carbon atoms;

$R^3$ hydrogen, a $C_1$–$C_4$-alkyl radical or one of the $R^2$ radicals.

The invention additionally relates to the novel fatty acids of the formula Ia

$$A^1\text{—}COOR^4 \qquad \qquad Ia$$

where $R^4$ is hydrogen or an alkali metal or ammonium cation of the corresponding fatty acid salt, and $A^1$ has the meaning stated at the outset, and to their use as surfactants. The invention further relates to surfactant formulations comprising compounds I or Ia.

DE-A 27 34 596 discloses fatty acid derivatives of type I as detersive substances for washing textiles.

For cleaning nontextile surfaces, surfactants must have additional properties such as good fat-removal capacities. Cleaning processes of this type take place mainly in the metal industry, in the food industry, in the catering trade and in the household. Thus, for example, it is often necessary to remove drawing and rolling greases from metal articles after processing thereof. The primary object in the other sectors mentioned is also in particular to remove fats of varying origin from equipment and containers, because fats prevent the wetting of other soiled particles.

It is an object of the invention to use surfactants for aqueous cleaner systems for cleaning nontextile material with an improved fat-removal capacity.

We have found that this object is achieved by using the amino hydroxy fatty acid derivatives I defined at the outset for cleaning nontextile grease-soiled materials, the compounds Ia as novel substances, and formulations containing I.

Compounds I can be obtained in a manner known per se by epoxidizing fatty acid esters III

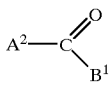

and further reaction of the epoxidized products IV with an amine V

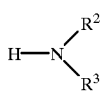

with opening of the epoxide ring. $A^2$ in this case is an unsaturated radical which corresponds to the saturated or partially saturated radical $A^1$ in I, and $B^1$ is the radical of a 1- to 3-hydric aliphatic $C_1$–$C_6$-alcohol. In the case of a polyhydric alcohol, its other hydroxyl groups may also be esterified, preferably with fatty acids.

Depending on the chosen ratio of III to V there is mainly reaction of the epoxide groups with the amine V. If there is an excess of amine, $B^1$ is replaced by the radical —$N(R^2)R^3$.

The esters obtained where appropriate in the reaction can be used, for example, to prepare the novel fatty acids or their alkali metal salts by known reactions such as alkaline hydrolysis and, if required, acidification.

The ammonium salts, which are likewise novel, can be obtained preferably directly from the epoxidized fatty acids by reaction with V. This results in the preferred ammonium salts with $^{\oplus}NH_2R^2R^3$ as cation, where $R^2$ and $R^3$ have the same meanings as in the amino group of the fatty acid ester. Any desired ammonium salts can be prepared by subsequent reaction of a fatty acid Ia' with an amine.

Among unsaturated unbranched aliphatic fatty acids from which the esters III are derived, the unsaturated hydroxy fatty acid ricinoleic acid is suitable, but preference is given to:

monounsaturated $C_9$–$C_{25}$-fatty acids such as petroselinic acid, undecenoic acid, $\Delta^9$-decylenic acid, $\Delta^9$-dodecylenic acid, vaccenic acid, palmitoleic acid, erucic acid and, in particular, oleic acid.

diunsaturated $C_9$–$C_{25}$-fatty acids such as stillingic acid, preferably linoleic acid.

triunsaturated fatty acids such as eleostearic and, preferably, linolenic acid.

Unsaturated $C_{18}$-fatty acids are particularly suitable because they are readily available. The acids obtainable by isomerization of the double bond are also suitable.

It is likewise possible to use mixtures of fatty acids or fatty acid esters like those obtainable, for example, by transesterification or hydrolysis of natural fats with $C_1$–$C_4$-alcohols.

The preparation of compounds I preferably starts from natural fats, ie. the glycerol esters comprising at least one unsaturated radical $A^2$. Examples of such natural fats are olive oil, cottonseed oil, linseed oil, tallow, fish oils, tall oils, castor oil, coconut oil, dodder oil, sunflower oil, peanut oil, palm oil, euphorbia oil and, in particular, soybean oil and rapeseed oil.

The epoxidation is carried out in a manner known per se by reacting compound III with peracids such as performic acid and peracetic acid. However, some epoxidized fatty acid esters IV are also commercially available.

The amines V are primary or secondary amines having at least one hydrophilic aliphatic $C_2$–$C_{40}$ radical. The amines may be branched and have several hydroxyl or amino groups, such as tris(hydroxymethyl)methylamine, but preferably have at least one unbranched ω-hydroxyalkyl radical or an ω-aminoalkyl radical having 2 to 6 carbon atoms, it being possible for the alkyl radical to be interrupted by nonadjacent oxygen atoms, —NH groups, N-$C_1$–$C_4$-alkyl groups or N-$C_1$–$C_4$-hydroxyalkyl groups. Also suitable are N-$C_1$–$C_4$-alkyl-substituted derivatives if they also contain at least one reactive amino or imino group. Suitable and preferred in this connection are:

hydroxyalkylamines such as mono- and diethanolamine, mono- and diisopropanolamine, 2-(2-aminoethoxy)ethanol, 2-(2-aminoethylamino)ethanol, 3-aminopropanol and N-alkyl-substituted hydroxyalkylamines such as methylethanolamine, n-propylethanolamine, butylethanolamine, 2-amino-1-butanol and, particularly preferably, aminopropyldiethanolamine.

aminoalkylamines such as ethylenediamine, trimethylenediamine, 1,2-propylenediamine, 3-amino-1-methylaminopropane, diethylenetriamine, dipropylenetriamine, N,N'-bis(3-amino-propyl)ethylenediamine, 3-(2-aminoethoxy)propylamine, 2-(2-aminoethoxy)ethylamine, 3-(3-aminopropoxy)propylamine and their symmetrically and asymmetrically N-substituted mono- and dialkyl derivates such as N,N-dimethylaminopropylamine, diethylaminoethylamine, diethylaminopropylamine, 1-diethylamino-4-aminopentane, neopentanediamine, hexamethylenediamine, 4,9-dioxadodecane-1,12-diamine, 4,7,10-trioxatridecane-1,13-diamine, 3-(2-aminoethyl)-aminopropylamine.

Amines which are likewise preferred and result in products with beneficial properties are polyalkylene glycol amines of the general formula VI

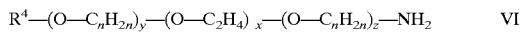

where
n is 2, 3 or 4
x is from 1 to 10
y and z are from 0 to 10
$R^4$ is hydrogen or a $C_1$–$C_4$-alkyl radical, having a total of 3 to 40, in particular 3 to 20 carbon atoms. These known amines are normally obtained by alkoxylating aliphatic $C_1$–$C_4$-alcohols or ethylene glycol and subsequently aminating. This alkoxylation can take place either with ethylene oxide, propylene oxide and/or butylene oxide or mixtures thereof.

Examples of suitable amines are methylglycolamine and methyltetraglycolamine.

The reaction of the epoxidized fatty acid esters, acids or their salts with the amines normally takes place at from 30 to 170° C., preferably in the presence of an alkaline catalyst such as alkali metal hydroxides, carbonates or alcoholates, for example sodium methoxide. The reaction is complete when epoxy groups are no longer detectable. The reaction is complete after about 2 to 4 hours at 100° C.

The reaction can be carried out in the presence of a solvent, but this is usually unnecessary, so that a solvent is preferably omitted.

The amine is generally employed in an amount which is from stoichiometric to 10 molar, preferably stoichiometric to 2.5 molar, relative to epoxy units. If epoxidized fatty acids are reacted, it is advisable to react with at least 2 equivalents of amine because part of the amine reacts to form the ammonium salt.

Stoichiometric reaction of the fatty acid esters with the amines results particularly in fatty acid esters as products, whereas reaction with 1.4 to 10 equivalents of the amine results predominantly in the fatty amides. A larger excess of amine is possible but in some circumstances means that it is subsequently necessary to remove the unreacted amine. Both the esters and the amides have, as nonionic surfactants, an excellent fat-dissolving capacity, while the fatty acid amides are somewhat more soluble in water. In addition, the acids and salts show a very good fat-dissolving capacity while being very soluble in water so that they are very suitable as anionic surfactants.

Reaction of the epoxidized compound IV with the amines V usually results in mixtures of isomers because the oxirane rings may open at both C—O bonds.

Reaction starting from natural fats results in a mixture which may contain not only compounds I but also glycerol and possibly the amides of saturated fatty acids. However, it is unnecessary to remove these substances for the use according to the invention because they do not interfere.

The amino hydroxy fatty acid derivatives I show, in use tests, good fat-dissolving properties as are required for surfactants in aqueous cleaning systems for nontextile surfaces. The surfactants I additionally show good foam-reduction behavior. The cleaning processes described at the outset are mainly carried out mechanically, for which the use of foam-reducing surfactants is important. Since vigorous circulation of water takes place in mechanical cleaning, otherwise a large amount of foam will be produced, which will weaken the mechanical cleaning power. Because of this exceptionally good foam-reduction behavior, the surfactants I are also suitable for use in compositions such as rinse aids for dishwashing machines, in which case the fat-removal capacity tends to be of low importance.

Besides the cleaning of kitchenware, the surfactants are also suitable for cleaning all nontextile surfaces which occur domestically and commercially, such as metal, painted wood, plastic or ceramic products, for example china, floor and wall tiles. The compositions can be applied for this purpose, for example, manually with a damp cloth or sponge or else by spray cleaning.

The compositions are normally marketed in the form of aqueous concentrates and can be used diluted or undiluted. Examples of conventional cleaners for nontextile surfaces are windshield cleaners, car shampoos, oven cleaners, window/imitation leather cleaners, plastics cleaners, toilet cleaners, scouring agents and bath cleaners.

The fatty acid derivatives I according to the invention are thus particularly suitable for aqueous cleaning systems for grease-soiled nontextile surfaces because, besides the good fat-removal capacity, they also effectively reduce foam. In this connection, it is particularly the nonionic surfactants, especially from the group of fatty amides, which are preferred for the use according to the invention. In addition, they can be obtained easily and have good biodegradability.

The water-based cleaner systems for cleaning nontextile materials comprise according to the invention surfactants I, their mixtures and, where appropriate, builders, solvents or solubilizers and other additives conventional for compositions of these types in the amounts conventional for the compositions. It is possible in this connection to use the surfactants I in combination with anionic or nonionic surfactants as mentioned, for example, in DE-A 27 34 597.

Very suitable rinse aids for dishwashing machines comprise, for example, 10 to 40, preferably 15 to 30, % by weight of I 5 to 30% by weight of a solubilizer such as alcohol or cumenesulfonate and 1 to 20% by weight of other conventional additives such as acids, for example citric acid or dicarboxylic acids.

A manual dishwashing composition consists, for example, of 5 to 50, preferably 5 to 30, % by weight of I 5 to 30% by weight of a solubilizer such as cumenesulfonate or alcohol and 0.5 to 5% by weight of skin-protecting agents, fragrances and dyes.

A composition according to the invention for a dip-degreasing composition for metal articles consists, for example, of 1 to 10, preferably 1 to 5, % by weight of I and 10 to 70% by weight of alkaline builders.

EXAMPLES

A. Preparation of Fatty Acid Derivatives I (Examples 1 to 5)

1 mol of an epoxidized fatty acid ester was added to a mixture of n mol of an amine V and 29 g of a 30% strength methanolic sodium methanolate solution while stirring at 80° C. The mixture was then stirred at 90–95° C. for 4 hours. The products were obtained as viscous liquids.

B. Use Properties of the Amino Hydroxy Fatty Acid Derivatives

The use properties of the amino hydroxy fatty acid derivatives I investigated were the fat-removal capacity, the cloud point, the foaming capacity, the surface tension and the foam reduction in a dishwashing machine of aqueous preparations.

To determine the fat-dissolving capacity, solid plates covered with engine oil or olive oil were dipped horizontally into the surfactant solution (c=1 g/l) to be investigated. The time until the first oil drop became detached from the particular plate was measured. A shorter time means a better fat-removal capacity.

The results of measurement of the fat-dissolving capacity of the substances of Examples 1 to 5 are to be found in Tables 1 and 2.

The cloud point was determined by the DIN 53917 method. This entailed determination of the temperature above which the solution becomes cloudy and is thus in the form of a mixture of two liquid phases. A lower cloud point means less foaming capacity.

The foaming capacity was determined by the DIN 53902 method by measuring the foam volume in ml one minute after ceasing to generate the foam.

The surface tension was determined by the DIN 53924 method by measuring the force in mN/m necessary to withdraw a plate or horizontally suspended ring from the surface of the liquid.

The foam-reduction behavior in the dishwashing machine was checked by the "egg test". Foam was generated in a commercial household dishwasher by adding an egg, and the average number of revolutions per minute of the spray arm during a twelve-minute heating phase was determined. The number of revolutions is reduced by foam formation because of the diminished repulse of force and thus represents a measure of the suitability of surfactants for cleaning machines.

The results of measurement on the substances of Examples 1 to 3 below are to be found in Table 3.

TABLE 1

| | | | | Fat-removal capacity at 40° C. [sec] Olive oil | | | | |
|---|---|---|---|---|---|---|---|---|
| Example No. | Fatty acid ester | Amine | n | Teflon | Poly-ethylene | Stainless steel | Ceramic | Glass |
| 1 | Rapeseed oil methyl ester | Aminopropyldi-ethanolamine | 1 | 15 | 20 | 66 | 10 | 5 |
| 2 | Rapeseed oil methyl ester | Aminopropyldi-ethanolamine | 2 | 2 | 50 | 6 | 2 | 2 |
| 3 | Soybean oil | Aminopropyldi-ethanolamine | 3 | 1 | 1 | 1 | 1 | 1 |
| 4 | Soybean oil | Aminopropyldi-ethanolamine | 6 | 7 | 18 | 3 | 2 | 3 |

TABLE 2

| Example No. | Fatty acid ester | Amine | n | Fat-removal capacity at 40° C. [sec] Engine oil | | | | |
|---|---|---|---|---|---|---|---|---|
| | | | | Teflon | Poly-ethylene | Stainless steel | Ceramic | Glass |
| 1 | Rapeseed oil methyl ester | Aminopropyldi-ethanolamine | 1 | 4 | 15 | 7 | 6 | 5 |
| 3 | Soybean oil | Aminopropyldi-ethanolamine | 3 | 5 | 10 | 20 | 56 | 6 |
| 5 | Rapeseed oil methyl ester | Diethanolamime | 2 | 2 | 20 | 50 | 20 | 2 |

TABLE 3

| Example No. | Cloud point (° C.) | Foaming capacity (ml) | Surface tension (nN/m) | Foam reduction (U/min) |
|---|---|---|---|---|
| 1 | 75.5 (BDG) | 5 | 32.7 | 88 |
| 2 | 44 (H₂O) | 40 | 32.9 | 19 |
| 3 | 33 (H₂O) | 40 | 32.4 | 31 |

BDG = Butyldiglycol

The present invention furthermore relates to alkoxylated fatty acid derivatives VII obtainable by reacting compounds VIII $$A^2\text{—CO—}R^5 \qquad \text{VIII,}$$

where the substituents have the following meanings:

$A^2$ an aliphatic $C_8$–$C_{24}$ radical with unbranched carbon chain, which chain contains one or more groups of the formula IX

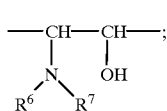  IX $R^5$ an —N($R^6$)$R^7$ radical, a hydroxyl radical and its alkali metal or ammonium salts, a $C_1$–$C_4$-alkoxy radical or a radical of a mono-, di- or triglyceride, where the di- or triglyceride radicals are radicals of natural saturated or unsaturated fatty acids or are identical or different radicals $A^2$, and $R^6$ and $R^7$ independently of one another hydrogen, an unsubstituted $C_1$–$C_6$-alkyl radical or a $C_1$–$C_{14}$-alkyl radical which is hydroxyl-, amino-substituted and/or aminocarbonyl-substituted, and/or can be interrupted by nonadjacent oxygen atoms, —NH groups and/or N-$C_1$–$C_4$-alkyl groups, and/or carries the radicals —COOH or —SO₃H and their alkali metal salts or ammonium salts, with from 3 to 15 equivalents of ethylene oxide, propylene oxide and/or butylene oxide per equivalent of IX.

The invention additionally relates to novel fatty acid derivatives VIIIa, the preparation of these fatty acid derivatives VII and VIIIa, their use as surfactants in detergents and cleaners, and formulations comprising these surfactants.

DE-A 16 19 081 discloses alkoxylation products of quaternary ammonium hydroxy fatty acid derivatives in fabric softeners.

Furthermore, DE-A 27 34 596 and DE-A 27 34 597 describe the use of amides and esters of aminohydroxystearic acid as detersive substances in hot and cold wash detergents.

EP-A-0 633 243 describes a process for preparing β-hydroxylated secondary and tertiary amines. The products obtained by reacting epoxidized olefins, such as epoxydodecane, with amino acids are surface-active substances and therefore suitable for numerous uses.

It is an object of the present invention to provide surfactants having advantageous properties.

We have found that this object is achieved by the alkoxylated fatty acid derivatives VII defined at the outset, the fatty acid derivatives VIIIa used as starting compounds, a process for preparing VII and VIIIa, their use as surfactants in detergents and cleaners, and formulations comprising VII or VIIIa.

The alkoxylated fatty acid derivatives VII are obtained by reacting VIII with from 3 to 15 equivalents of ethylene oxide, propylene oxide and/or butylene oxide per equivalent of IX. The compounds VIII in this case usually contain a plurality of reactive groups, but at least one hydroxyl group, which can undergo alkoxylation. The hydroxyl, —NH, —NH₂ and carboxyl radicals of $R^5$, $R^6$ and $R^7$ which are present where appropriate are likewise alkoxylated. Moreover, insertion by alkylene oxide is observed in the case of ester groups. Since compounds VIII are reacted with at least three moles of alkylene oxide per mole of VIII, mixtures of products are obtained. As a rule, it is wished to obtain water-soluble compounds which also have good lipophilic properties and vice versa. Mixtures having good hydrophilic properties are obtained by reacting at least 3 equivalents, and those having good lipophilic properties are obtained by reacting not more than 12 equivalents, of alkylene oxide per equivalent of IX.

The compounds are preferably reacted with ethylene oxide and/or propylene oxide, particularly preferably with ethylene oxide, because these products have particularly good biodegradability. Reaction with a plurality of alkylene oxides can take place successively or directly using a mixture.

The reaction takes place under known alkoxylation conditions, preferably in the presence of an alkaline catalyst such as potassium hydroxide, sodium hydroxide, sodium methanolate or potassium tertiary butoxide. It is possible to carry out the reaction under either atmospheric or superatmospheric pressure, preferably under a pressure of 1–20 bar, particularly preferably 1.5–10 bar. In an advantageous embodiment moreover, the alkylene oxide is added in portions.

The reaction takes place even at room temperature but is preferably carried out at 80–120° C. and, above 150° C., affords mixtures with a higher proportion of alkoxylated amino groups. Depending on the chosen temperatures, the reaction takes from 0.5 to 10 hours, lower temperatures requiring a longer reaction time and vice versa.

It is possible to use inert solvents such as toluene or xylene, but it is more advantageous not to use additional solvent because it is unnecessary to remove the solvent.

The fatty acid derivatives VIII employed are compounds of the general formula VIII $$A^2\text{—CO—}R^5 \qquad \qquad \text{VIII}$$

having the radicals defined above. The compounds VIII can be obtained in a manner known per se by epoxidation of fatty acids, their salts or esters

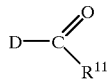

XI and further reaction of the epoxidized products X with an amine XII

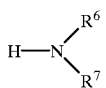

XII with opening of the epoxide ring. D in this case is an unsaturated radical which corresponds to the saturated or partially saturated radical $A^2$ in VIII, and $R^{11}$ is a hydroxyl radical and its alkali metal or ammonium salts or the radical of a 1- to 3-hydric aliphatic $C_1$–$C_6$-alcohol. In the case of a polyhydric alcohol, its other hydroxyl groups may also be esterified, preferably with fatty acids.

$R^{11}$ can moreover likewise be replaced by the radical —$N(R^6)R^7$.

The esters or amides obtained where appropriate in the reaction can be used to prepare the fatty acids and their alkali metal salts for example by known reactions such as alkaline hydrolysis and, if required, acidification.

The ammonium salts can be obtained preferably directly from the epoxidized fatty acids by reaction with XII. This results in the preferred ammonium salts with $^{\oplus}NHR^6R^7$ as cation where $R^6$ and $R^7$ have the same meanings as in the amino group of the fatty acid ester. Any desired ammonium salts can be prepared by subsequent reaction of a fatty acid VIII with an amine.

Among unsaturated unbranched aliphatic fatty acids from which the epoxidized fatty acid derivatives X are derived, the unsaturated hydroxy fatty acid ricinoleic acid is suitable, but preference is given to monounsaturated $C_9$–$C_{25}$-fatty acids such as petroselinic acid, undecenoic acid, $\Delta^9$-decylenic acid, $\Delta^9$-dodecylenic acid, vaccenic acid, palmitoleic acid, erucic acid and, in particular, oleic acid diunsaturated $C_9$–$C_{25}$-fatty acids such as stillingic acid, preferably linoleic acid triunsaturated fatty acids such as eleostearic and preferably linolenic acid.

Unsaturated $C_{18}$-fatty acids are particularly suitable because they are readily available.

Also suitable are the acids obtainable by isomerization of the double bond.

It is equally possible to use mixtures of fatty acids or fatty acid esters which can be obtained, for example, by transesterification or hydrolysis of natural fats with $C_1$–$C_4$-alcohols, preferably methanol.

The compounds VII are preferably prepared starting from natural fats, ie. the glycerol esters comprising at least one unsaturated radical D. Examples of such natural fats are olive oil, cottonseed oil, linseed oil, tallow, fish oils, tall oils, castor oil, coconut oil, hempseed oil, sperm oil, lard, goose fat, beef tallow, neatsfoot oil, tallow fatty acid, dodder oil, sunflower oil, peanut oil, palm oil, euphorbia oil and, especially, soybean oil and rapeseed oil.

The epoxidation is carried out in a manner known per se by reacting the compound XI with peracids such as performic acid and peracetic acid. However, some epoxidized fatty acid derivatives X are also commercially available.

The amides XI comprise ammonia, primary or secondary amines having an unsubstituted $C_1$–$C_6$-alkyl radical or a substituted $C_1$–$C_{14}$-alkyl radical.

The amines may be branched and have several hydroxyl or amino groups, such as tris(hydroxymethyl)methylamine, but preferably have at least one unbranched ω-hydroxyalkyl radical or an ω-aminoalkyl radical having 2 to 6 carbon atoms, it being possible for the alkyl radical to be interrupted by nonadjacent oxygen atoms, NH groups or N-$C_1$–$C_4$-alkyl groups. Also suitable are the N-$C_1$–$C_4$-alkyl-substituted derivatives if they also contain at least one reactive amino or imino group.

Suitable aliphatic amines are short-chain secondary amines, eg. $C_1$–$C_6$-alkylamines such as dimethylamine, diethylamine, dipropylamine, dibutylamine, the corresponding mixed amines, for example methylethylamine, and primary amines, eg. $C_1$–$C_6$-alkylamines such as methylamine, ethylamine, propylamine, butylamine, pentylamine and hexylamine, and branched amines, for example isopropylamine. Of these, preference is given to the reaction products VIII of the primary amines because these contain an imino group which can be alkoxylated.

Suitable substituted amines are preferably the reaction products VIII of the following amines:

hydroxyalkylamines such as mono- and diethanolamine, mono- and diisopropanolamine, 2-(2-aminoethoxy)ethanol, 2-(2-aminoethylamino)ethanol, 3-aminopropanol, aminopropyldiethanolamine, aminosorbitol, glucamine and N-alkyl-substituted hydroxyalkylamines such as methylethanolamine, n-propylethanolamine, butylethanolamine, N-methylglucamine and 2-amino-1-butanol, aminoalkylamines such as ethylenediamine, trimethylenediamine, 1,2-propylenediamine, 3-amino-1-methylaminopropane, diethylenetriamine, dipropylenetriamine, N,N'-bis(3-amino-propyl)ethylenediamine, 3-(2-aminoethoxy)propylamine, 2-(2-aminoethoxy)ethylamine, 3-(3-aminopropoxy)propylamine and their symmetrically and asymmetrically substituted mono- and dialkyl derivatives such as N,N-dimethylaminopropylamine, diethylaminoethylamine, diethylaminopropylamine, 1-diethyl-amino-4-aminopentane, neopentanediamine, hexamethylenediamine, 4,9-dioxadodecane-1,12- diamine, 4,7,10-trioxatridecane-1,13-diamine, 3-(2-aminoethyl)aminopropylamine.

The amines may also be amino acids.

Reaction of the epoxidized fatty acid derivatives with the amino acid results in the novel fatty acid derivatives of the general formula VIIIa

   VIIIa where the substituents have the following meanings:

$A^3$ an aliphatic $C_8$–$C_{24}$ radical with unbranched carbon chain, which chain contains one or more groups of the formula IXa

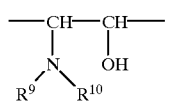   IXa $R^8$ an —$N(R^6)R^7$ radical, a hydroxyl radical and its alkali metal or ammonium salts, a $C_1$–$C_4$-alkoxy radical or a radical of a mono-, di- or triglyceride, it being possible for the two latter to be radicals of natural saturated or unsaturated fatty acids or identical or different radicals $A^3$, and $R^9$ a $C_1$–$C_6$-alkyl radical which may be hydroxyl-, amino-substituted and/or aminocarbonyl-substituted and/or may be interrupted by nonadjacent NH groups and carries an —$SO_3H$ radical or at least one —COOH radical, and their alkali metal salts or ammonium salts, and $R^{10}$ hydrogen or one of the $R^9$ radicals.

Amino acids $NHR^9R^{10}$ mean in this connection aliphatic carboxylic acids or sulfonic acids with amino and/or imino groups. The carboxylic or sulfonic acids are preferably unbranched. They may furthermore have other acid or amide groups and be substituted by hydroxyl radicals. In this connection it is irrelevant to the effect of VII and VIIIa whether D or L forms or mixtures are used. The known amino acids are, as a rule, easily available, for example by a Strecker reaction. Moreover, many are commercially available. Examples of suitable amino acids are:

monocarboxylic acids such as valine, leucine, isoleucine, ornithine, citrulline, serine, threonine, preferably alanine, arginine, lysine, particularly preferably glycine and sarcosine dicarboxylic acids such as asparagine, aspartic acid, glutamine, glutamic acid, particularly preferably imi-nodiacetic acid and ethylenediaminediacetic acid tricarboxylic acids such as carboxymethylaspartic acid and sulfonic acids such as N-methyltaurine and taurine.

The epoxidized fatty acid esters, fatty acids or their salts are, as a rule, reacted with the amines at from 30 to 280° C., preferably 80 to 140° C., preferably in the presence of an alkaline catalyst such as alkali metal hydroxides, carbonates or alcoholates, for example sodium methoxide. The reaction is complete when epoxy groups are no longer detectable. For example, the reaction is complete after 2 to 4 hours at 120° C.

The reaction can be carried out in the presence of a solvent, but this is usually unnecessary so that a solvent is preferably omitted.

If the amines are not liquids but solids, such as the amino acids, they are preferably reacted as suspension in water-soluble or partly water-soluble solvents. Suitable examples are polyhydric alcohols and, in particular, glycerol, ethylene glycol and propylene glycol, because they can subsequently remain in the product. Since, as a rule, the amino acid is present partly as solution and partly undissolved, in a preferred embodiment the Na salt of the amino acid is introduced, for example, into propylene glycol with the basic catalyst, and the epoxidized compound XI is metered in. Advantageous temperatures for this reaction are from 60 to 200° C., in particular 100 to 180° C.

Another advantageous process starting from solid amines is reaction in the melt. The temperatures necessary for this are those at which the mixture is in the form of a type of melt, which may perfectly well be below the solidification point of the amino acid itself, as a rule above 200° C. Depending on the onset of decomposition of the amino acids, the preferred upper temperature range is from 220 to 260° C. In an advantageous embodiment, the amino acid is dissolved in a little water and heated together with the base and the epoxidized fatty acid or its ester. The high temperatures result in immediate evaporation of the water so that the reaction mixture is in the form of a melt.

The amine is generally employed in an amount which is from stoichiometric to 5 molar, preferably 2.5 molar, relative to epoxy units. If epoxidized fatty acids are reacted, it is advisable to react with at least two equivalents of amine because part of the amine reacts to form the ammonium salt.

Reaction of the fatty acid esters with the amines results, on reaction with 1.4 to 5 equivalents of the amine, in particular in the fatty amides as products. A larger excess of amine is possible but, in some circumstances, makes it necessary subsequently to remove the unreacted amine.

Reaction of the epoxidized compound X with the amines XII usually results in mixtures of isomers because opening of the oxirane rings is possible at both C—O bonds.

Reaction starting from natural fats results in a mixture which may contain not only compounds VIII but also glycerol and possibly the amides of saturated fatty acids. However, it is unnecessary to remove these substances for the subsequent alkoxylation because they do not interfere.

It has been found according to the invention that the products VIIIa of the reaction of epoxidized fatty acid derivatives with amino acids result in compounds with good surface-active properties, which are therefore outstandingly suitable for use as anionic surfactants in detergents and cleaners. Low surface and interfacial tensions have been found in tests. In addition, they show good fat-dissolving capacity and a good single wash cycle performance.

In addition, synergistic effects on the single wash cycle performance can be observed in combination with nonionic surfactants such as $C_{13/15}$ oxo alcohol with 7 mol of ethylene oxide and exceed the previously disclosed effects with mixtures of anionic and nonionic surfactants.

Good properties of the compounds VIIIa are observed even with the fatty acid esters. The acids and their salts show a better effect. However, they are even exceeded by the fatty amides because of the better solubility.

The alkoxylated amino hydroxy fatty acid derivatives VII show good fat-dissolving properties in use tests. These fat-dissolving properties are a very important requirement in cleaners for hard surfaces because, in general, fats prevent the wetting of other soiled particles. The fat-dissolving capacity of a surfactant is equally important for laundering textiles. Surfactants with such properties often have low solubility in water, which is shown by low cloud points.

The compounds VII according to the invention show not only a good fat-dissolving power but, at the same time, higher cloud points, so that they are suitable, for example, as surfactant in a heavy duty detergent.

The alkoxylated amino hydroxy fatty acid derivatives described above are employed in detergents alone or in combination with at least one anionic and/or nonionic surfactant, usually in an amount of from 2 to 50, preferably 8 to 30, % by weight, based on the total weight of the particular formulation.

The detergents can be in powder form or else in liquid formulation. The composition of detergents and cleaners may vary greatly. Detergent and cleaner formulations normally contain from 2 to 50% by weight of surfactants, with or without builders. These data apply both to liquid and to powder detergents. Detergent and cleaner formulations customary in Europe, the USA and Japan are tabulated, for example, in Chemical and Engn. News, 67 (1989) 35. Further details of the composition of detergents and cleaners can be found in Ullmanns Enzyklopädie der technischen Chemie, Verlag Chemie, Weinheim 1983, 4th Edition, pages 63 to 160.

Reduced phosphate detergents mean formulations which contain no more than 25% by weight of phosphate calculated as pentasodium triphosphate. The detergents may be heavy duty detergents or specialty detergents. Suitable surfactants are both anionic and nonionic, or mixtures of anionic and nonionic, surfactants. The surfactant content of the detergents is preferably 8 to 30% by weight.

Examples of suitable anionic surfactants are fatty alcohol sulfates from fatty alcohols with 8 to 22, preferably 10 to 18, carbon atoms, eg. $C_9$–$C_{11}$ alcohol sulfates, $C_{12}$–$C_{13}$ alcohol sulfates, cetyl sulfate, myristyl sulfate, palmityl sulfate, stearyl sulfate and tallow fatty alcohol sulfate.

Further suitable anionic surfactants are sulfated, ethoxylated $C_8$–$C_{22}$ alcohols and their soluble salts. Compounds of this type are prepared, for example, by initially alkoxylating a $C_8$–$C_{22}$, preferably a $C_{10}$–$C_{18}$, alcohol and subsequently sulfating the product of the alkoxylation. Ethylene oxide is preferably used for the alkoxylation, in which case 2 to 50, preferably 3 to 20, mol of ethylene oxide are employed per mole of fatty alcohol. The alcohols can, however, also be alkoxylated with propylene oxide, alone or with butylene oxide. Also suitable are alkoxylated $C_8$–$C_{22}$ alcohols which contain ethylene oxide and propylene oxide or ethylene oxide and butylene oxide. The alkoxylated $C_8$–$C_{22}$ alcohols may contain the ethylene oxide, propylene oxide and butylene oxide units in the form of blocks or in random distribution.

Further suitable anionic surfactants are alkylsulfonates such as $C_8$–$C_{24}$—, preferably $C_{10}$–$C_{18}$—, alkanesulfonates, and soaps such as the salts of $C_8$–$C_{24}$ carboxylic acids.

Further suitable anionic surfactants are linear $C_9$–$C_{20}$-alkyl-benzenesulfonates (LAS). The fatty acid derivatives according to the invention are preferably employed in detergent formulations with less than 4% by weight of LAS, particularly preferably in LAS-free formulations.

The anionic surfactants are preferably added in the form of salts to the detergent. Suitable cations in these salts are alkali metal ions such as sodium, potassium or lithium ions, and ammonium ions such as hydroxyethylammonium, di(hydroxyethyl)-ammonium and tri(hydroxyethyl) ammonium ions.

Examples of suitable nonionic surfactants are alkoxylated $C_8$–$C_{22}$ alcohols. The alkoxylation can be carried out with ethylene oxide, propylene oxide and/or butylene oxide. It is possible to employ as surfactant in this case all alkoxylated alcohols which contain at least two molecules of one of the abovementioned alkylene oxides in the adduct. Also suitable in this case are block copolymers of ethylene oxide, propylene oxide and/or butylene oxide, or adducts which contain said alkylene oxides in random distribution. From 2 to 50, preferably 3 to 20, mol of at least one alkylene oxide are used per mole of alcohol. Ethylene oxide is preferably employed as alkylene oxide. The alcohols preferably have 10 to 18 carbon atoms.

Another class of nonionic surfactants comprises alkyl polyglucosides with 8 to 22, preferably 10 to 18, carbon atoms in the alkyl chain. These compounds contain 1 to 20, preferably 1.1 to 5, glucoside units.

Another class of nonionic surfactants comprises N-alkylglucamides of the general structure XIII or XIV

(XIII)

(XIV)

where Y is $C_6$–$C_{22}$-alkyl, X is H or $C_1$–$C_4$-alkyl and Z is a poly-hydroxyalkyl radical with 5 to 12 carbon atoms and at least 3 hydroxyl groups. Y is preferably $C_{10}$–$C_{18}$-alkyl, X is preferably $CH_3$ and Z is preferably a $C_5$ or $C_6$ radical. Compounds of this type are obtained, for example, by acylation of reductively aminated sugars with chlorides of $C_{10}$–$C_{18}$-carboxylic acids. The detergent formulations preferably contain $C_{10}$–$C_{16}$ alcohols ethoxylated with 3–12 mol of ethylene oxide, particularly preferably ethoxylated fatty alcohols, as nonionic surfactants.

Further suitable and preferred surfactants are the end group-capped fatty amide alkoxylates which are disclosed in WO-A-95/11225 and have the general formula

where $L^1$ is $C_5$–$C_{21}$-alkyl or -alkenyl, $L^2$ is $C_1$–$C_4$-alkyl,

A is $C_2$–$C_4$-alkylene, n is 2 or 3, and x has a value from 1 to 6.

Examples of such compounds are the products of the reaction of n-butyltriglycolamine of the formula $H_2N$—$(CH_2$—$CH_2$—$O)_3$—$C_4H_9$ with methyl dodecanoate or the products of the reaction of ethyltetraglycolamine of the formula $H_2N$—$(CH_2$—$CH_2$—$O)_4$—$C_2H_5$ with a commercial mixture of saturated $C_8$–$C_{18}$ fatty acid methyl esters.

The detergents in powder or granule form and, where appropriate, structured liquid detergents additionally contain one or more inorganic builders. Suitable inorganic builder substances are all conventional inorganic builders such as aluminosilicates, silicates, carbonates and phosphates.

Examples of suitable inorganic builders are aluminosilicates with ion-exchanging properties such as zeolites. Various types of zeolites are suitable, in particular zeolites A, X, B, P, MAP and HS in their Na form or in forms in which Na is partly replaced by other cations such as Li, K, Ca, Mg or ammonium. Suitable zeolites are described, for example, in EP-A 0 038 591, EP-A 0 021 491, EP-A 0 087 035, U.S. Pat. No. 4,604,224, GB-A 2 013 259, EP-A 0 522 726, EP-A 0 384 070A and WO-A 94/24251.

Examples of other suitable inorganic builders are amorphous or crystalline silicates such as amorphous disilicates, crystalline disilicates such as the sheet silicate SKS-6 (manufactured by Hoechst AG). The silicates can be employed in the form of their alkali metal, alkaline earth metal or ammonium salts. Na, Li and Mg silicates are preferably employed.

Further suitable inorganic builders are carbonates and bicarbonates. These can be employed in the form of their alkali metal, alkaline earth metal or ammonium salts. Preferably employed are Na, Li and Mg carbonates and bicarbonates, in particular sodium carbonate and/or sodium bicarbonate.

The inorganic builders may be present in the detergents in amounts of from 0 to 60% by weight together with organic cobuilders which are to be used where appropriate. The inorganic builders can be incorporated either alone or in any combination with one another into the detergent. In detergents in powder or granule form, they are added in amounts of from 10 to 60% by weight, preferably in amounts of from 20 to 50% by weight. In structured (multiphase) liquid detergents, inorganic builders are added in amounts of up to 40% by weight, preferably up to 20% by weight. They are suspended in the liquid formulation ingredients.

Detergent formulations in powder or granule form, and liquid detergent formulations contain organic cobuilders in amounts of from 0.1 to 20% by weight, preferably in amounts of from 1 to 15% by weight, together with inorganic builders. The heavy duty detergents in powder or granule form may additionally contain, as other conventional ingredients, a bleaching system consisting of at least one bleach, where appropriate in combination with a bleach activator and/or a bleach catalyst.

Suitable bleaches are perborates and percarbonates in the form of their alkali metal, in particular their Na, salts. They are present in the formulations in amounts of from 5 to 30% by weight, preferably 10 to 25% by weight. Other suitable bleaches are inorganic and organic peracids in the form of their alkali metal or magnesium salts or partly also in the form of the free acids. Examples of suitable per-carboxylic acids and salts thereof are Mg monoterephthalate, phthalimidopercaproic acid and diperdodecanedioic acid. An example of an inorganic peracid salt is potassium peroxomonosulfate (Oxon).

Examples of suitable bleach activators are
acylamines such as tetraacetylethylenediamine, tetraacetylglycoluril, N,N'-diacetyl-N,N'-dimethylurea and 1,5-diacetyl-2,4-dioxohexahydro-1,3,5-triazine,
acylated lactams such as acetylcaprolactam, octanoylcaprolactam and benzoylcaprolactam,
substituted phenol esters of carboxylic acids such as Na acetoxybenzenesulfonate, Na octanoyloxybenzenesulfonate and Na nonanoyloxybenzenesulfonate,
acylated sugars such as pentaacetylglucose,
anthranil derivatives such as 2-methylanthranil or 2-phenyl-anthranil,
enol esters such as isopropenyl acetate,
oxime esters such as acetone O-acetyloxime,
carboxylic anhydrides such as pththalic anhydride or acetic anhydride.

The bleach activators preferably employed are tetraacetylethylenediamine and Na nonanoyloxybenzenesulfonates. The bleach activators are added to heavy duty detergents in amounts of from 0.1 to 15% by weight, preferably in amounts of from 1.0 to 8.0% by weight, particularly preferably in amounts of from 1.5 to 6.0% by weight.

Suitable bleach catalysts are quaternized imines and sulfone imines as described in U.S. Pat. No. 5,360,568, U.S. Pat. No. 5,360,569 and EP-A 0 453 003, and Mn complexes, cf., for example, WO-A 94/21777. If bleach catalysts are employed in the detergent formulations, they are present therein in amounts of up to 1.5% by weight, preferably up to 0.5% by weight, and in the case of the very active manganese complexes in amounts of up to 0.1% by weight.

The detergents preferably contain an enzyme system. This comprises proteases, lipases, amylases and cellulases normally employed in detergents. The enzyme system may be limited to a single enzyme or comprise a combination of different enzymes. The detergents contain the commercial enzymes as a rule in amounts of from 0.1 to 1.5% by weight, preferably 0.2 to 1.0% by weight, of the formulated enzyme. Examples of suitable proteases are Savinase® and Esperase® (manufactured by Novo Nordisk). An example of a suitable lipase is Lipolase® (manufactured by Novo Nordisk). An example of a suitable cellulase is Celluzym® (manufactured by Novo Nordisk).

The detergents contain as other conventional ingredients preferably soil release polymers and/or antiredeposition agents. These comprise, for example,
polyesters from polyethylene oxides with ethylene glycol and/or propylene glycol and aromatic dicarboxylic acids or aromatic and aliphatic dicarboxylic acids, or polyesters from polyethylene oxides with di- and/or polyhydric alcohols and dicarboxylic acids, which are endgroup-capped at one end. Polyesters of these types are known, cf., for example, U.S. Pat. No. 3,557,039, GB-A 1 154 730, EP-A 0 185 427, EP-A 0 241 984, EP-A 0 241 985, EP-A 0 272 033 and U.S. Pat. No. 5,142,020.

Other suitable soil release polymers are amphiphilic graft or other copolymers of vinyl and/or acrylic esters on polyalkylene oxides (cf. U.S. Pat. No. 4,746,456, U.S. Pat. No. 4,846,995, DE-A 3 711 299, U.S. Pat. No. 4,904,408, U.S. Pat. No. 4,846,994 and U.S. Pat. No. 4,849,126) or modified celluloses such as methylcellulose, hydroxypropylcellulose or carboxymethylcellulose.

Antiredeposition agents and soil release polymers are present in the detergent formulations in amounts of from 0 to 2.5% by weight, preferably 0.2 to 1.5% by weight, particularly preferably 0.3 to 1.2% by weight. Soil release polymers which are preferably employed are the graft copolymers, disclosed in U.S. Pat. No. 4,746,456, of vinyl acetate on polyethylene oxide of molecular weight 2500–8000 in the ratio of 1.2:1 to 3.0:1 by weight, and commercial polyethylene terephthalate/polyoxyethylene terephthalates of molecular weight 3000 to 25,000 from polyethylene oxides of molecular weight 750 to 5000 with terephthalic acid and ethylene oxide and a molar ratio of polyethylene terephthalate to polyoxyethylene terephthalate of from 8:1 to 1:1, and the block polycondensates which are disclosed in DE-A 4 403 866 and which contain blocks of (a) ester units from polyalkylene glycols having a molecular weight of 500 to 7500 and aliphatic dicarboxylic acids and/or monohydroxy monocarboxylic acids and (b) ester units from aromatic dicarboxylic acids and polyhydric alcohols. These amphiphilic block copolymers have molecular weights of from 1500 to 25,000.

A typical heavy duty detergent in powder or granule form may have, for example, the following composition:

2–50, preferably 8–30, % by weight of at least one of the anionic and/or nonionic surfactants described above, 5–50, preferably 15–42.5, % by weight of at least one inorganic builder, 5–30, preferably 10–25, % by weight of an inorganic bleach, 0.1–15, preferably 1–8, % by weight of a bleach activator, 0–1, preferably a maximum of 0.5, % by weight of a bleach catalyst, 0.05–5% by weight, preferably 0.2 to 2.5% by weight, of a color transfer inhibitor based on water-soluble homopolymers of N-vinylpyrrolidone or N-vinylimidazole, water-soluble copolymers of N-vinylimidazole and N-vinylpyrrolidone, crosslinked copolymers of N-vinylimidazole and N-vinylpyrrolidone with a particle size of from 0.1 to 500, preferably up to 250 μm, these copolymers containing 0.01 to 5, preferably 0.1 to 2, % by weight of N,N'-divinylethyleneurea as crosslinker; other color transfer inhibitors are water-soluble and cross-linked polymers of 4-vinylpyridine N-oxide obtainable by polymerizing 4-vinylpyridine and subsequently oxidizing the polymers;

0.1–20, preferably 1–15, % by weight of at least one organic cobuilder, 0.2–1.0% by weight of protease, 0.2–1.0% by weight of lipase, 0.3–1.5% by weight of a soil release polymer.

A bleach system is often completely or partly dispensed with in mild specialty detergents (for example in color detergents). A typical color detergent in powder or granule form may have, for example, the following composition:

2–50, preferably 8–30, % by weight of at least one of the anionic and/or nonionic surfactants described above, 10–60, preferably 20–55, % by weight of at least one inorganic builder, 0–15, preferably 0–5, % by weight of an inorganic bleach, 0.05–5% by weight, preferably 0.2–2.5% by weight, of a color transfer inhibitor (cf. above), 0.1–20, preferably 1–15, % by weight of at least one organic cobuilder, 0.2–1.0% by weight of protease, 0.2–1.0% by weight of cellulase, 0.2–1.5% by weight of a soil release polymer, eg. a graft copolymer of vinyl acetate on polyethylene glycol.

The detergents in powder or granule form may contain as other conventional ingredients up to 60% by weight of inorganic fillers. Sodium sulfate is normally used for this purpose. However, the detergents according to the invention preferably have a low filler content of up to 20% by weight, particularly preferably up to 8% by weight of fillers.

The detergents according to the invention may have apparent densities varying in the range from 300 to 950 g/l. Modern compact detergents as a rule have higher apparent densities, eg. 550 to 950 g/l, and a granular structure.

The novel liquid detergents contain, for example:

5–60, preferably 10–40, % by weight of at least one of the anionic and/or nonionic surfactants described above, 0.05–5% by weight, preferably 0.2–2.5% by weight, of a color transfer inhibitor (cf. above), 0.1–20, preferably 1–15, % by weight of at least one cobuilder, 0–1.0% by weight of protease, 0–1.0% by weight of cellulase, 0–1.5% by weight of a soil release polymer and/or anti-redeposition agent, 0–60% by weight of water, 0–10% by weight of alcohols, glycols such as ethylene glycol, diethylene glycol or propylene glycol, or glycerol.

The detergents may where appropriate contain further conventional additives. Further additives which may be present are, for example, complexing agents, phosphonates, optical brighteners, dyes, perfume oils, foam suppressants and corrosion inhibitors.

By cleaners for hard surfaces are meant, for example, cleaners for metals, plastics, glass and ceramics, floor cleaners, toilet cleaners, all-purpose cleaners for household and commercial applications, industrial cleaners (for use in car washing systems or high-pressure cleaners), low temperature cleaners, dishwashing agents, manual dishwashing agents, rinse aids, disinfecting cleaners, cleaners for the foodstuff and beverage industries, in particular as bottle cleaners, CIP cleaners (cleaning-in-place) in dairies, breweries and other foodstuff manufacturing plants. Cleaners which comprise surfactants according to the invention are particularly suitable for cleaning hard surfaces such as glass, plastic and metal. The cleaners may be adjusted to be alkaline, acidic or neutral. They normally contain surfactants in amounts of about 5–90, preferably 10–75, % by weight, based on the active substance content. These may comprise anionic, nonionic or cationic surfactants, and mixtures of surfactants which are mutually compatible, eg. mixtures of anionic and nonionic or of cationic and nonionic surfactants. Alkaline cleaners may contain sodium carbonate, potassium carbonate, sodium bicarbonate, potassium bicarbonate, sodium sesquicarbonate, potassium sesquicarbonate, sodium hydroxide, potassium hydroxide, amine bases such as monoethanolamine, diethanolamine, triethanolamine, ammonia or silicate in amounts of up to 60% by weight, and in some cases even up to 80% by weight. The cleaners may additionally contain citrates, gluconates or tartrates in amounts of up to 80% by weight. They may be in solid or in liquid form.

The surfactants VII and VIIIa are also suitable as dye penetration aids in leather dyeing.

The percentage data in the examples mean % by weight unless otherwise evident therefrom.

EXAMPLES

A. Preparation of the Amino Hydroxy Fatty Acid Derivatives VIII (general method)

1 mol of an epoxidized fatty acid ester was added to a mixture of n mol of an amine and 29 g of a 30% strength methanolic sodium methanolate solution with stirring at 80° C. The molecular weight was determined by titrating the epoxide and/or from the saponification number. If both amide formation and epoxide opening are required, an average molecular weight from epoxide number/saponification number was used as basis. The mixture was then stirred at 90–95° C. for 4 hours. The reaction products were obtained as viscous liquids.

Example 6

A mixture of 111 g (1 mol) of sodium sarcosinate and 14.4 g of a 30% strength solution of sodium methanolate (0.08 mol) in methanol was suspended in 123 g of propylene glycol. At 160° C., 152.8 g (0.5 mol) of epoxidized rapeseed oil methyl ester were metered in. The mixture was then stirred at 160–170° C. for 7 hours.

Example 7

3.6 g (0.09 mol) of sodium hydroxide dissolved in 3.6 g of water and 152.8 g (0.5 mol) of epoxidized rapeseed oil methyl ester were added to a solution of 111 g (1 mol) of sodium sarcosinate in 150 ml of water. The mixture was heated with stirring at 240° C. for 5 hours. The reaction product was obtained as a beige solid.

Example 8

18.0 g (0.23 mol, 50% by weight) of sodium hydroxide solution were added to a solution of 22.5 g (0.3 mol) of glycine in 33 ml of water so that the pH was adjusted to 9–10. 47.3 g (0.15 mol) of epoxidized rapeseed oil methyl ester were added dropwise to this. The solution was heated with stirring to 107–115° C., and the water was distilled out over the course of 80 min. The pH was kept at 9–10 with 2 g (0.025 mol, 50% by weight) of sodium hydroxide solution. The mixture was then stirred at 230° C. for 6 h. The reaction product was obtained as a pale beige solid.

Example 9

15.6 g (0.2 mol, 50% by weight) of sodium hydroxide solution were added to a solution of 26.6 g (0.2 mol) of iminodiacetic acid in 30 ml of water so that the pH was adjusted to 9–10. 31.5 g (0.1 mol) of epoxidized rapeseed oil methyl ester were added dropwise to this. The solution was heated with stirring to 102–115° C., and the water was distilled out over the course of 1 h. The pH was kept at 9–10 with 2.5 g (0.03 mol, 50% by weight) of sodium hydroxide solution. The mixture was then stirred at 230° C. for 8 h. The reaction product was obtained as a grayish beige solid.

B. Preparation of the Alkoxylated Fatty Acid Derivatives VII (Examples 10 to 14)

The derivatives VIII obtained by the general method or the particular embodiment of Example 7 were reacted with m mol of ethylene oxide (equivalent to k mol per epoxy unit originally present) in the presence of 1% by weight of potassium hydroxide (based on VIII) at 100–110° C. in a pressure vessel under 1.4 to 5.9 bar. The addition took 5 hours, and the mixture was then stirred for a further 4 hours. The compounds according to the invention were obtained in the form of yellow pastes. (The number of epoxy units was determined by titration.)

C. Use Properties

The use properties of the amino hydroxy fatty acid derivatives VIII and alkoxylation products VII investigated were the fat-removal capacity, the cloud point, the foaming capacity and the surface tension of aqueous formulations.

To determine the fat-removal capacity, solid plates covered with engine oil or olive oil are immersed horizontally in the surfactant solution (c=1 g/l) to be investigated. The time until the first oil drop is removed from the particular plate is measured. A shorter time means a better fat-removal capacity.

The results of measurement of the fat-dissolving capacity of the substances of Examples 6, 7 and 10 to 14 are to be found in Table 4.

The cloud point was determined by the DIN 53917 method. This entails measurement of the temperature above which the solution becomes cloudy and is thus in the form of a mixture of two liquid phases. A lower cloud point generally means a lower foaming capacity.

The foaming capacity was determined by the DIN 53902 method by measuring the foam volume in ml one minute after the end of foam generation.

The surface tension was determined by the DIN 53914 method, by measuring the force in mN/m necessary to pull a plate or a horizontally suspended ring out of the liquid surface.

The results of measurements on the substances of the examples are to be found in Table 5.

TABLE 4

| | | | | | Fat-removal capacity at 40° C. [sec] Olive oil | | | |
|---|---|---|---|---|---|---|---|---|
| Ex. No. | Fatty acid ester | Amine | n | m (k) | Teflon | Stainless steel | Ceramic | Glass |
| 6 | Rapeseed oil methyl ester | Sarcosine | 2 | — | 340 | 260 | 420 | 27 |
| 7 | Rapeseed oil methyl ester | Sarcosine | 2 | — | 50 | 120 | 49 | 26 |

TABLE 4-continued
| Ex. No. | Fatty acid ester | Amine | n | m (k) | Fat-removal capacity at 40° C. [sec] Olive oil | | | |
|---|---|---|---|---|---|---|---|---|
| | | | | | Teflon | Stainless steel | Ceramic | Glass |
| 10 | " | Ethanolamine | 2 | 6 | 4 | 425 | 120 | 14 |
| 11 | " | " | 2 | 3 | 4 | 53 | 64 | 27 |
| 12 | Soybean oil | Ethanolamine | 6 | 18 (6) | 13 | 14 | 90 | 1 |
| 13 | Soybean oil | Ethylenediamine | 6 | 18 (6) | 6 | 18 | 15 | 3 |
| 14 | Rapeseed oil methyl ester | Sarcosine | 2 | 6 | 266 | 165 | 100 | 92 |
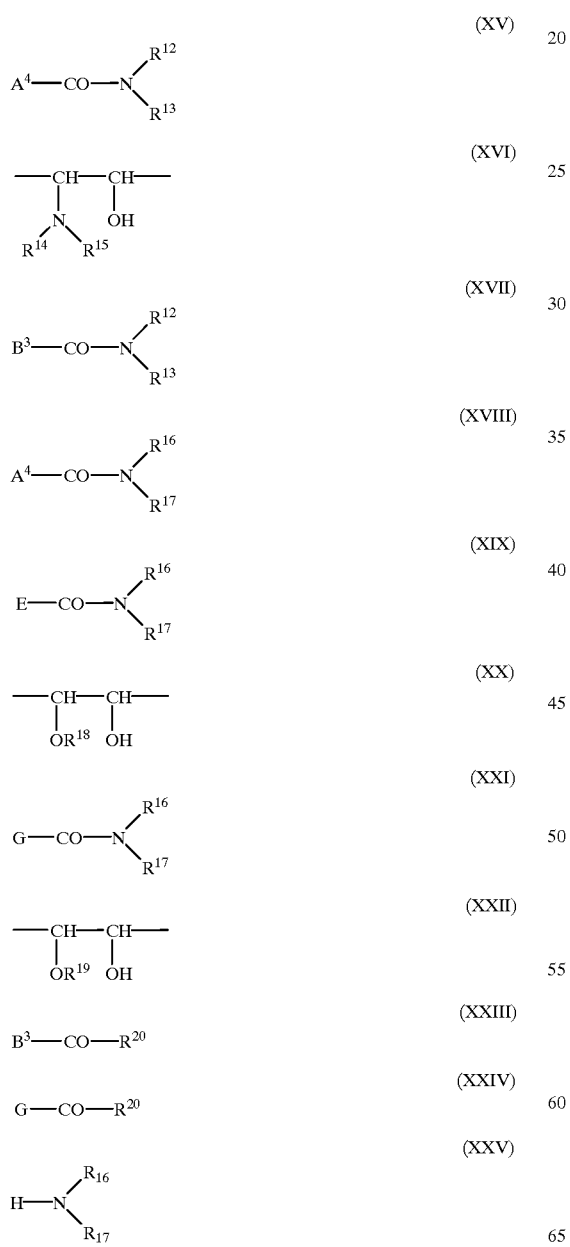

TABLE 7

Detergent compositions A–P

| Ingredients | A | B | C | D | E | F | G | H | I | J | K | L | M | N | O | P |
|---|---|---|---|---|---|---|---|---|---|---|---|---|---|---|---|---|
| Linear alkylbenzenesulfonate | | | 6 | 6 | 1 | 8 | 9 | 7.5 | | | | | | 2.5 | | 7.5 |
| $C_{12}$–$C_{18}$-alkyl sulfate | 9 | 9 | 2 | 3 | 12 | | | 1.5 | 10 | 9 | 9 | 9 | 9 | 5 | 9 | 2 |
| $C_{12}$-fatty alcohol × 2 EO sulfate | | | | | | | | | 3 | | | | | | 2 | |
| $C_{12}$–$C_{18}$-fatty alcohol × 4 EO | | | | | | | | 3 | 4.5 | | | 4 | 4 | | | |
| $C_{12}$–$C_{18}$-fatty alcohol × 7 EO | 10 | 10 | | | | | | | | | | | | 13.5 | | 4 |
| $C_{13}$–$C_{15}$ oxo alcohol × 7 EO | | | 7 | | 5 | 8 | 10 | | | 10 | 10 | | | | | |
| $C_{13}$–$C_{15}$ oxo alcohol × 11 EO | | | | 4.5 | | | | 3 | | | | | | 2 | 7 | |
| $C_{16}$–$C_{18}$-glucamide | | | | | | | | | 4 | | | | | | | |
| $C_{12}$–$C_{14}$-alkyl polyglucoside | | | | | | | | | | | | | 4 | | | |
| $C_8$–$C_{18}$ fatty acid methyl tetraglycolamide | | | | | | | | | | | | 6 | | | | |
| Soap | 2 | 2 | 1 | | 0.5 | 2 | 0.5 | 0.6 | 1 | 2 | 2 | 2 | 2 | 1.5 | 2 | |
| Na metasilicate × 5.5 $H_2O$ | 2 | 2 | 3.5 | | | 3 | | | | 2 | 2 | 2 | 2 | | | |
| Na silicate | | | | 8 | | | 2.5 | 4 | | | | | | 0.5 | | |
| Mg silicate | | | | | 0.8 | | | | | | | | 0.5 | | | |
| Zeolite A | 18 | 24 | 36 | 35 | 15 | 30 | 36.5 | 25 | 20 | 36 | 24 | 36 | 36 | | 55 | 25 |
| Zeolite P | 18 | | | | | | | | | | | | | | 36 | |
| Sheet silicate SKS 6 (Hoechst AG) | | 12 | | | 14 | | | | 12 | | | | | | | |
| Amorphous sodium disilicate | | | | | | | | | | 12 | 12 | | | | | |
| Sodium carbonate | 12 | 12 | 12 | 11 | | 15 | 10.5 | 10 | 8 | | | 12 | 12 | | 6 | |
| Sodium bicarbonate | | | | | 9 | | | | | | | | | 6.5 | | |
| Sodium citrate | | | | | 5 | | | 7 | 4 | | | | | | | 4 |
| TAED | 4 | 4 | 3.5 | 3.5 | 5.5 | 3 | 4 | 3.8 | 5 | 4 | 4 | 4 | 4 | | | |
| Perborate 4 $H_2O$ | | | 15 | 20 | | 20 | | | 24 | | | | | | | |
| Perborate 2 $H_2O$ | | | | | | | 14.5 | | | | | | | | | |
| Percarbonate | 15 | 15 | | | 18 | | | | 20 | 15 | 15 | 15 | 15 | | | |
| Carboxymethylcellulose | 1 | 1 | 1.5 | 2.5 | 0.5 | 2 | 1 | 1.3 | 1.5 | 1 | 1 | 1 | 1 | 1 | 1 | |
| Soil release Additive 1 | 0.8 | 0.8 | 0.8 | | 0.5 | | | 0.5 | 0.5 | | | 0.5 | 0.5 | 0.5 | | |
| Soil release Additive 2 | | | | | | | | | | | | 0.5 | 0.5 | | | |
| Lipase | | | | | 0.2 | 0.5 | | 0.5 | 0.5 | | | 0.5 | 0.5 | | | 0.5 |
| Protease | | | | | 0.5 | 0.5 | | 0.5 | 0.5 | | | 0.5 | 0.5 | | 1 | 0.5 |
| Cellulase | | | | | 0.3 | | | | | | | 0.2 | | | | 0.2 |
| Sodium sulfate | 3 | 3 | 3 | 1.5 | 3.5 | 3 | 3.5 | 2.4 | | 3 | 3 | 2.4 | 1.3 | 2 | | |
| Cobuilder 1 | 5 | 5 | 5 | 5 | 5 | 5 | 8 | 5 | 5 | 5 | 5 | 5 | 5 | 5 | 5 | 15 |
| Phosphonate | | | | | | | | | 0.2 | | | | 0.2 | | | 0.5 |
| Opt. brightener | 0.2 | 0.2 | 0.2 | | 0.2 | | | 0.2 | 0.2 | | | 0.2 | 0.2 | | | 0.2 |
| Color transfer inhibitor | | | | | | | | | | | | | | 1.5 | 1 | |
| Water | | | 3.5 | | 3.5 | | | | 0.3 | 1 | 1 | 1 | | 22.5 | 11 | 40.6 |

Cobuilder 1 $\hat{=}$ AA/MA (acrylic acid/maleic acid) copolymer MW 70000

TABLE 5

| Ex. No. | Cloud point [° C.] | Foaming capacity [ml] | Surface tension [mN/m] |
|---|---|---|---|
| 6 | >100 | 220 | 41 |
| 7 | >100 | 370 | 44 |
| 10 | 52 | 70 | 33.5 |
| 11 | 61 | 90 | 35 |

The surfactants VIIIa according to the invention were tested under standard conditions (60° C., 5 g/l, addition of 19% VIIIa) in model detergent formulation A without other surfactants.

In addition, the surfactants according to the invention of Examples 8 and 9 were, in combination with a nonionic surfactant, tested in a model detergent formulation A without other surfactants under standard conditions (60° C., 5 g/l, addition of 19% of which 38.6% is VIIIa and 61.4% is $C_{13/15}$ oxo alcohol with 7 mol of ethylene oxide).

The washing tests were carried out under the following conditions:

| | |
|---|---|
| Washing machine | Atlas Launder-O-meter |
| Wash cycles | 1 |
| Rinse cycles | 1 |
| Washing temperature | 60° C. |
| Washing time | 30 min. |
| Water hardness | 3 mmol/l |
| Ca:Mg | 4:1 |
| Amount of liquor | 250 ml |
| Detergent concentration | 5 g/l |
| Soiled fabric | WFK 10 D, WFK 20 D Test fabrics from WfK-Testgewebe GmbH EMPA 101, EMPA 104 Test fabrics from Eidgenössische Materialprüfanstalt St. Gallen |
| Detergent formulation A: | |
| Zeolite A | 30% |
| Sodium carbonate | 12% |
| Sodium silicate | 3% |
| Tylose CR 1500 p | 1.2% |
| Sodium perborate monohydrate | 14.4% |
| Tetraacetylethylenediamine | 4% |
| Acrylic acid/maleic acid copolymer MW 70000 | |
| Soap | 0.5% |
| Sodium sulfate | 4% |
| Water | 6.9% |
| Surfactant according to the invention | 19% (or 19% of a mixture of 61.4% surfactant according to the invention and 38.6% $C_{13/15}$ oxo alcohol with 7 mol of ethylene oxide = 7 EO) |

Rinsing was followed by spinning, and the fabrics were hung up individually to dry. The fabric was measured with an Elrepho 2000 from Data Color, Heidenheim, specifically 6 points being measured on each piece of fabric. The reflectance was determined at 480 nm.

Table 6 summarises the values for the total reflectance R and the average single wash cycle performance.

TABLE 6

| Anionic surfactant | Nonionic surfactant | Reflectance (Σ R) |
|---|---|---|
| — | — | 139.7 |
| — | $C_{13/15}$ oxo alcohol with 7 EO | 192.2 |
| Dodecylbenzenesulfonate | — | 168.7 |
| Dodecylbenzenesulfonate | $C_{13/15}$ oxo alcohol with 7 EO | 184.9 |
| Glycine + rapeseed oil methyl ester (2:1) Example 8 | — | 169.8 |
| Iminodiacetic acid + rapeseed oil methyl ester (2:1) Example 9 | — | 152.0 |
| Glycine + rapeseed oil methyl ester (2:1) | $C_{13/15}$ oxo alcohol with 7 EO | 205.7 |
| Iminodiacetic acid + rapeseed oil methyl ester (2:1) | $C_{13/15}$ oxo alcohol with 7 EO | 218.5 |

The surfactants according to the invention can be employed in the following examples of detergent formulations.

The present invention furthermore relates to fatty amide derivatives with amide groups having nonionic hydrophilic substituents and with amine groups having anionic substituents in the fatty acid chain or with amide groups having anionic substituents and with amine groups having nonionic hydrophilic substituents in the fatty acid chain. The invention furthermore relates to a process for preparing these fatty amide derivatives via corresponding epoxidized fatty amides and to such epoxidized fatty amides themselves as intermediates for the preparation of surfactants. The invention furthermore relates to mixtures of fatty amide derivatives with amine groups in the fatty acid chain and those with alkoxy groups in the fatty acid chain. The present invention also relates to detergents and cleaners which comprise said fatty amide derivatives or said mixtures of fatty amide derivatives as surfactants.

DE-A 27 34 596 and DE-A 27 34 597 disclose the use of amides and esters of aminohydroxystearic acid as detersive substances in hot and cold wash detergents.

EP-A 0 633 243 describes a process for preparing β-hydroxylated secondary and tertiary amines. The products obtained by reacting epoxidized olefins such as epoxydodecane with amino acids are surface-active substances and therefore suitable for numerous uses.

U.S. Pat. No. 3,155,658 discloses the reaction of epoxy carboxamides with amines. The resulting products are suitable as corrosion inhibitors, mineral oil additives and ore flotation aids.

It is an object of the present invention to provide surfactants with an even more advantageous range of properties than prior art surfactants.

We have found that this object is achieved by fatty amide derivatives of the general formula XV

(XV)

in which the substituents have the following meanings:

$A^4$ an aliphatic $C_8$–$C_{24}$ radical with unbranched carbon chain, which chain contains one or more groups of the formula XVI

(XVI)

$R^{12}$ a hydroxyl- and/or amino-substituted hydrophilic radical having 2 to 40 carbon atoms, $R^{13}$ hydrogen, an unsubstituted $C_1$–$C_6$-alkyl radical or a radical $R^{12}$, $R^{14}$ a $C_1$–$C_{14}$-alkyl radical which has carboxyl and/or sulfo groups in the form of the free acids and/or their alkali metal or ammonium salts and which may be interrupted by nonadjacent oxygen atoms, —NH groups and/or N-$C_1$–$C_4$-alkyl groups, $R^{15}$ hydrogen, an unsubstituted $C_1$–$C_6$-alkyl radical or a radical $R^{14}$, where the meaning of the two pairs of substituents $R^{12}/R^{13}$ and $R^{14}/R^{15}$ may also be interchanged.

Among unsaturated unbranched aliphatic fatty acids from which the fatty amide derivatives XV are derived, ricinoleic acid as the unsaturated hydroxy fatty acid is suitable, but preference is given to monounsaturated $C_9$–$C_{25}$-fatty acids such as petroselinic acid, undecenoic acid, Δ9-decylenic acid, Δ9-dodecylenic acid, vaccenic acid, palmitoleic acid, erucic acid, elaidic acid and, in particular, oleic acid, diunsaturated $C_9$–$C_{25}$-fatty acids such as stillingic acid and, in particular, linoleic acid, and triunsaturated $C_9$–$C_{25}$-fatty acids such as eleostearic and, in particular, linolenic acid.

Unsaturated $C_{18}$-fatty acids are particularly suitable because they are readily available.

Also suitable are fatty acids obtainable by isomerization of the double bond.

The fatty amide derivatives XV according to the invention may also be based on mixtures, in particular naturally occurring mixtures of such fatty acids.

The amines $HN(R^{12})R^{13}$ which underlie the amide groups in XV and have one or two nonionic hydrophilic substituents may be branched and have several hydroxyl or amino groups, such as tris(hydroxymethyl)methylamine, but preferably have at least one unbranched ω-hydroxyalkyl group or one unbranched ω-aminoalkyl group having, in each case, 2 to 6 carbon atoms, it being possible for the underlying alkyl group to be interrupted by nonadjacent oxygen atoms, NH groups, N-$C_1$–$C_4$-alkyl groups, N-$C_1$–$C_4$-hydroxyalkyl groups or N-$C_1$–$C_4$-aminoalkyl groups. Also suitable are N-$C_1$–$C_4$-alkyl-substituted derivatives if they also contain at least one reactive amino or imino group.

Particularly suitable amines of these types are the following:

hydroxyalkylamines such as mono- and diethanolamine, mono- and diisopropanolamine, 2-(2-aminoethoxy)ethanol, 2-(2-aminoethylamino)ethanol, 3-aminopropanol, aminopropyldiethanolamine, aminosorbitol, glucamine and N-alkyl-substituted hydroxyalkylamines such as methylethanolamine, n-propylethanolamine, butylethanolamine, N-methylglucamine and 2-amino-1-butanol, aminoalkylamines such as ethylenediamine, trimethylenediamine, 1,2-propylenediamine, 3-amino-1-methylaminopropane, diethylenetriamine, dipropylenetriamine, N,N'-bis(3-aminopropyl)ethylenediamine, 3-(2-aminoethoxy)propylamine, 2-(2-aminoethoxy)ethylamine, 3-(3-aminopropoxy)propylamine and their symmetrically and asymmetrically substituted mono- and dialkyl derivatives such as N,N-dimethylaminopropylamine, diethylaminoethylamine, diethylaminopropylamine, 1-diethylamino-4-aminopentane, neopentanediamine, hexamethylenediamine, 4,9-dioxadodecane-1,12-diamine, 4,7,10-trioxatridecane-1,13-diamine and 3-(2-aminoethylamino)propylamine.

The amines $HN(R^{14})R^{15}$ which underlie the amine groups in the fatty acid chain in XV and have one or two anionic substituents are amino or imino carboxylic acids ("amino acids") or amino or imino sulfonic acids, with amino acids being particularly preferred. These carboxylic and sulfonic acids are preferably unbranched. They may furthermore have other acid or amide groups and be substituted by hydroxyl radicals. In this connection it is irrelevant to the effect whether D or L forms or mixtures thereof, eg. racemates, are used. The known amino acids are, as a rule, easily available, for example, by a Strecker reaction. Many of the amino acids are commercially available. Examples of suitable amino acids are:

monocarboxylic acids such as valine, leucine, isoleucine, ornithine, citrulline, serine, threonine, especially alanine, arginine, lysine, in particular glycine and sarcosine, dicarboxylic acids such as asparagine, aspartic acid, glutamine, glutamic acid, in particular iminodiacetic acid and ethylenediaminediacetic acid, tricarboxylic acids such as carboxymethylaspartic acid and sulfonic acids such as N-methyltaurine and taurine.

If the radicals $R^{13}$ and/or $R^{15}$ are $C_1$–$C_6$-alkyl, they mean propyl, isopropyl, butyl, isobutyl, sec-butyl, tert-butyl, pentyl, isopentyl, sec-pentyl, tert-pentyl, neopentyl, hexyl or, in particular, methyl or ethyl.

The fatty amide derivatives XV according to the invention are advantageously prepared by reacting an epoxidized fatty amide of the formula XVII

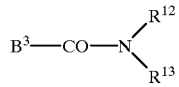

(XVII)

where $B^3$ is an aliphatic $C_8$–$C_{24}$ radical with unbranched carbon chain, which chain contains one or more epoxy groups, with at least one equivalent of amine of the formula $HN(R^{14})R^{15}$ per epoxy unit, where the substituents $R^{12}$ to $R^{15}$ have the abovementioned meanings.

Reaction of the epoxidized fatty amides XVII with the amines $HN(R^{14})R^{15}$ usually takes place at from 20 to 280° C., in particular 50 to 200° C., especially 80 to 180° C., as a rule under atmospheric pressure and preferably in the presence of a basic catalyst, for example an alkali metal hydroxide, alkali metal carbonate or alkali metal alcoholate such as sodium methoxide, sodium ethoxide or potassium tert-butoxide. The reaction is complete when epoxy groups are no longer detectable.

Reaction of the epoxidized fatty amides XVII with said amines usually results in mixtures of isomers because opening of the oxirane rings is possible at both C—O bonds.

The epoxidized fatty amides XV themselves can be obtained by reacting corresponding epoxidized fatty acid esters, fatty acids or their salts with the amines $HN(R^{12})R^{13}$. The conditions employed for this are in principle the same in respect of temperature, pressure, catalysts present and other reaction parameters as for the reaction of the epoxidized fatty amides XVII with the amines $HN(R^{14})R^{15}$.

The epoxidized fatty acid esters, fatty acids or their salts employed as starting materials can be prepared by epoxidizing corresponding unsaturated fatty acid esters, fatty acids or their salts by conventional methods. This epoxidation is usually carried out in a conventional way by reaction with peracids such as performic acid and peracetic acid. Some epoxidized fatty acid esters or fatty acids are, however, also commercially available.

The epoxidized fatty acid esters or fatty acids are preferably prepared starting from natural fats, ie. glycerol esters, especially triglycerides, which contain at least one unsaturated fatty acid residue. Examples of such natural fats are olive oil, cottonseed oil, linseed oil, tallow, fish oils, tall oils, castor oil, coconut oil, hempseed oil, sperm oil, lard, goose fat, beef tallow, neatsfoot oil, tallow fatty acid, dodder oil, sunflower oil, peanut oil, palm oil, euphorbia oil and, especially, soybean oil and rapeseed oil. However, it is likewise possible to use fatty acid or fatty acid ester mixtures as obtainable, for example, by transesterification or hydrolysis of natural fats with $C_1$–$C_4$ alcohols, preferably methanol.

Reaction of the epoxidized fatty acid esters or fatty acids with the amines $HN(R^{12})R^{13}$ and reaction of the epoxidized fatty amides XVII with the amines $HN(R^{14})R^{15}$ can in each case be carried out in the presence of a solvent, but this is often unnecessary so that frequently a solvent can be dispensed with.

If the amines $HN(R^{12})R^{13}$ or $HN(R^{14})R^{15}$ are not liquids but solids such as, for example, the amino acids, they can be reacted as suspension in water-soluble or partly water-soluble solvents. Suitable examples are polyhydric alcohols and, in particular, glycerol, ethylene glycol and propylene glycol, because they can subsequently remain in the product. Since, as a rule, the amino acid is present partly as solution and partly undissolved, in a preferred embodiment the Na salt of the amino acid is introduced, for example, into propylene glycol with the basic catalyst, and the reactant is metered in; advantageous reaction temperatures in this case are from 60 to 200° C., in particular 100 to 180° C. It is also possible to employ said amines, especially the amino acids, as purely aqueous solutions in the reaction. In another preferred embodiment, the Na salt of the amino acid is added as solid to the reaction mixture.

Another advantageous process starting from solid amines, eg. amino acids, is reaction in the melt. The temperatures necessary for this are those at which the mixture is in the form of a type of melt, which may perfectly well be below the solidification point of the amino acid itself, as a rule above 200° C. Depending on the onset of decomposition of the amino acids, the preferred upper temperature range is 220 to 260° C. In an advantageous embodiment, the amino acid is dissolved in a little water and heated together with the base and the epoxidized fatty acid or its ester. The high temperatures result in immediate evaporation of the water so that the reaction mixture is in the form of a melt.

The epoxidized fatty acid esters, epoxidized fatty acids or their salts are, as a rule, reacted with one or approximately one equivalent of amine $HN(R^{12})R^{13}$ per carboxylic acid unit. The present invention also relates to a process of this type for preparing the epoxidized fatty amides XVII. The amine reacts only or very predominantly with the ester or carboxylic acid functionality to form an amide, while the epoxy group is completely or virtually completely retained. If epoxidized fatty acids are employed in the acid form, it is advisable to react with up to two equivalents of amine because part of the amine reacts to form the ammonium salt.

The epoxidized fatty amides XVII are reacted with at least one equivalent of amine $HN(R^{14})R^{15}$ per epoxy unit, and 1 to 2.5, in particular 1 to 1.3, equivalents of amine per epoxy unit are preferred.

A very particularly preferred procedure is one in which the reaction of the epoxidized fatty acid esters or fatty acids with the amines $HN(R^{12})R^{13}$ and the subsequent reaction of the resulting epoxidized fatty amides XVII with the amines $HN(R^{14})R^{15}$ is carried out in a two-stage "one-pot" synthesis, ie. in the same reaction vessel without intermediate isolation. Thus, for example, epoxidized fatty acid lower alkyl esters or epoxidized triglycerides can be reacted with hydroxylamines or aminoalkylamines with alcoholate catalysis to give the corresponding epoxidized fatty amides XVII, and subsequently the fatty amide derivative XV can be prepared therefrom with the solid Na salt of an amino acid or with an aqueous solution of such a salt. It is also possible, for example, to react epoxidized fatty acid lower alkyl esters or epoxidized triglycerides with the Na salt of an amino acid in solution or suspension to give the corresponding epoxidized fatty amides XVII, and subsequently prepare the fatty amide derivative XV therefrom by further reaction with hydroxyalkylamines or aminoalkylamines.

The epoxidized fatty amides XVII described thus represent a central intermediate in the route to the fatty amide derivatives XV. However, it is possible to prepare, starting from the compounds XVII, not only the final products XV which are suitable as surfactants but also surfactants with a different structure, obtainable by reacting the compounds XVII with all possible types of N, S, O or C nucleophiles to open the oxirane ring. Examples of such N, S, O or C nucleophiles and other nucleophiles which can be used are the following:

N nucleophiles: amines (eg. $NH_3$, hexamethylenetetramine), amino acids, aminoacetonitriles (eg. RNH—CHR'—CN), amides, ureas, thioureas, imides, hydroxylamines (eg. $H_2NOH$), hydrazines (eg. $H_2NNH_2$), hydrazides (eg. $RCONHNH_2$), cyanamides (eg. RNH—CN), nitrocyanamides (eg. $NaN(NO_2)CN$), isocyanide ($^{-I}$ N≡C), nitrate, nitrite ($NO_2^-$), azide ($N_3^-$), nitrones, N-oxides, cyanates, isocyanates (NCO-), isothiocyanate, guanidines, cyanoguanidine, formamidine;

O nucleophiles: alcohols (eg. $C_1$–$C_8$-alkanols, also polyhydric alcohols such as ethylene glycol, glycerol), sugars (eg. glucose, sucrose), carboxylates (eg. acetates, formates, oxalates, lactates, maleates) and the corresponding free acids, water, hydroxide ($OH^-$), hydroperoxide ($OOH^-$), phenolates;

S nucleophiles: bisulfite ($HSO_3^-$), sulfite ($SO_3^{2-}$), thiocyanate ($SCN^-$), isothiocyanate, $S_2^{2-}$, mercaptans ($HS^-$, $RS^-$), $S_2O_3^{2-}$;

C nucleophiles: cyanide, carbanions or enolates, eg. of ketones, esters, acids, also of nitriles and nitro compounds, 1,3-dicarbonyl compounds (eg. malonic esters, β-keto esters) and their analogs, such as malononitrile (NC—$CH_2$—CN), enamines, imines and their iminium salts (eg. $H_2C\!\!=\!\!NH_2^+$), cyanohydrins, acetylides (R—C≡$C^-$), 1,3-dithianes;

other nucleophiles: phosphonates, borates and the corresponding free acids, $LiAlH_4$ and other $H^-$donors, halides.

R and R' in said compounds are organic radicals.

Accordingly, the present invention also relates to epoxidized fatty amides of the general formula XVII

in which the substituents have the following meanings:

$B^3$ an aliphatic $C_8$–$C_{24}$ radical with unbranched carbon chain, which chain contains one or more epoxy groups, $R^{12}$ a hydroxyl- and/or amino-substituted hydrophilic radical having 2 to 40 carbon atoms or a $C_1$–$C_{14}$-alkyl radical which has carboxyl and/or sulfo groups in the form of the free acids and/or their alkali metal or ammonium salts and which may be interrupted by nonadjacent oxygen atoms, —NH groups and/or N-$C_1$–$C_4$-alkyl groups, and $R^{13}$ hydrogen, an unsubstituted $C_1$–$C_6$-alkyl radical or a radical $R^{12}$, as intermediates for the preparation of surfactants.

It has been found, according to the invention, that the fatty amide derivatives XV have excellent surface-active properties and are thus outstandingly suitable for use as anionic surfactants in detergents and cleaners. Low surface and interfacial tensions have been found in tests. In addition, they show a good fat dissolving capacity and a good single wash cycle performance. The extremely advantageous profile of properties of these surfactants is explained mainly by the balance between nonionic hydrophilic and anionic substituents in XV.

The present invention therefore also relates to detergents and cleaners which comprise the fatty amide derivatives XV according to the invention as surfactants in amounts conventional for this purpose, and other additives conventional for compositions of this type.

Furthermore, synergistic effects are to be observed in combination with nonionic surfactants, such as alkoxylated long-chain alcohols, eg. $C_{13/15}$ oxo alcohol with 7 mol of ethylene oxide, in the single wash cycle performance, and these exceed effects previously disclosed for mixtures of anionic and nonionic surfactants. In some cases there are also synergistic effects with anionic surfactants, eg. with fatty alcohol sulfonates or fatty alcohol ester sulfates.

The fatty amide derivatives XV show good fat-dissolving properties in use tests. These fat-dissolving properties are a very important requirement for cleaners for hard surfaces because, in general, fats prevent the wetting of other soil particles. The fat-dissolving capacity of a surfactant is equally important for laundering textiles. Surfactants with such properties often have low solubility in water, which is shown by low cloud points.

The compounds XV according to the invention show not only a good fat-dissolving power but, at the same time, higher cloud points, so that they are suitable, for example, as surfactant in a heavy duty detergent.

The compounds XV are employed in detergents alone or in combination with at least one anionic and/or nonionic surfactant, usually in an amount of from 2 to 50, preferably 8 to 30, % by weight, based on the total weight of the particular formulation.

The detergents can be in powder form or else in liquid formulation. The composition of detergents and cleaners may vary greatly. Detergent and cleaner formulations normally contain from 2 to 50% by weight of surfactants, with or without builders. These data apply both to liquid and to powder detergents. Detergent and cleaner formulations customary in Europe, the USA and Japan are tabulated, for example, in Chemical and Engn. News, 67 (1989) 35. Further details of the composition of detergents and cleaners can be found in Ullmanns Enzyklopädie der technischen Chemie, Verlag Chemie, Weinheim 1983, 4th edition, pages 63 to 160.

Reduced phosphate detergents mean formulations which contain no more than 25% by weight of phosphate calculated as pentasodium triphosphate. The detergents may be heavy duty detergents or specialty detergents. Suitable surfactants are both anionic and nonionic, or mixtures of anionic and nonionic, surfactants. The surfactant content of the detergents is preferably 8 to 30% by weight.

Examples of suitable anionic surfactants are fatty alcohol sulfates from fatty alcohols with 8 to 22, preferably 10 to 18, carbon atoms, eg. $C_9$–$C_{11}$ alcohol sulfates, $C_{12}$–$C_{13}$ alcohol sulfates, cetyl sulfate, myristyl sulfate, palmityl sulfate, stearyl sulfate and tallow fatty alcohol sulfate.

Further suitable anionic surfactants are sulfated, ethoxylated $C_8$–$C_{22}$ alcohols and their soluble salts. Compounds of this type are prepared, for example, by initially alkoxylating a $C_8$–$C_{22}$, preferably a $C_{10}$–$C_{18}$, alcohol and subsequently sulfating the product of the alkoxylation. Ethylene oxide is preferably used for the alkoxylation, in which case 2 to 50, preferably 3 to 20, mol of ethylene oxide are employed per mole of fatty alcohol. The alcohols can, however, also be alkoxylated with propylene oxide, alone or with butylene oxide. Also suitable are alkoxylated $C_8$–$C_{22}$ alcohols which contain ethylene oxide and propylene oxide or ethylene oxide and butylene oxide. The alkoxylated $C_8$–$C_{22}$ alcohols may contain the ethylene oxide, propylene oxide and butylene oxide units in the form of blocks or in random distribution.

Further suitable anionic surfactants are alkylsulfonates such as $C_8$–$C_{24}$-, preferably $C_{10}$–$C_{18}$-, alkanesulfonates, and soaps such as the salts of $C_8$–$C_{24}$ carboxylic acids.

Further suitable anionic surfactants are linear $C_9$–$C_{20}$-alkyl-benzenesulfonates (LAS). The fatty acid derivatives according to the invention are preferably employed in detergent formulations with less than 4% by weight of LAS, particularly preferably LAS-free formulations.

The anionic surfactants are preferably added in the form of salts to the detergent. Suitable cations in these salts are alkali metal ions such as sodium, potassium or lithium ions, and ammonium ions such as hydroxyethylammonium, di(hydroxyethyl)-ammonium and tri(hydroxyethyl) ammonium ions.

Examples of suitable nonionic surfactants are alkoxylated $C_8$–$C_{22}$ alcohols. The alkoxylation can be carried out with ethylene oxide, propylene oxide and/or butylene oxide. It is possible to employ as surfactant in this case all alkoxylated alcohols which contain at least two molecules of one of the abovementioned alkylene oxides in the adduct. Also suitable in this case are block copolymers of ethylene oxide, propylene oxide and/or butylene oxide, or adducts which contain said alkylene oxides in random distribution. From 2 to 50, preferably 3 to 20, mol of at least one alkylene oxide are used per mole of alcohol. Ethylene oxide is preferably employed as alkylene oxide. The alcohols preferably have 10 to 18 carbon atoms.

Another class of nonionic surfactants comprises alkyl polyglucosides with 8 to 22, preferably 10 to 18, carbon atoms in the alkyl chain. These compounds contain 1 to 20, preferably 1.1 to 5, glucoside units.

Another class of nonionic surfactants comprises N-alkylglucamides of the general structure XIII or XIV

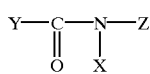

(XIII)

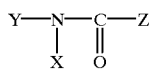

(XIV)

where Y is $C_6$–$C_{22}$-alkyl, X is H or $C_1$–$C_4$-alkyl and Z is a poly-hydroxyalkyl radical with 5 to 12 carbon atoms and at least 3 hydroxyl groups. Y is preferably $C_{10}$–$C_{18}$-alkyl, X is preferably $CH_3$ and Z is preferably a $C_5$ or $C_6$ radical. Compounds of this type are obtained, for example, by acylation of reductively aminated sugars with chlorides of $C_{10}$–$C_{18}$-carboxylic acids. The detergent formulations preferably contain $C_{10}$–$C_{16}$ alcohols ethoxylated with 3–12 mol of ethylene oxide, particularly preferably ethoxylated fatty alcohols, as nonionic surfactants.

Further suitable and preferred surfactants are the end group-capped fatty amide alkoxylates which are disclosed in WO-A-95/11225 and have the general formula

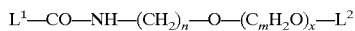

where $L^1$ is $C_5$–$C_{21}$-alkyl or -alkenyl, $L^2$ is $C_1$–$C_4$-alkyl, m is 2, 3 or 4, n is 2 or 3, and x has a value from 1 to 6.

Examples of such compounds are the products of the reaction of n-butyltriglycolamine of the formula $H_2N$—$(CH_2$—$CH_2$—$O)_3$—$C_4H_9$ with methyl dodecanoate or the products of the reaction of ethyltetraglycolamine of the formula $H_2N$—$(CH_2$—$CH_2$—$O)_4$—$C_2H_5$ with a commercial mixture of saturated $C_8$–$C_{18}$ fatty acid methyl esters.

The detergents in powder or granule form and, where appropriate, structured liquid detergents additionally contain one or more inorganic builders. Suitable inorganic builders are all conventional inorganic builders such as aluminosilicates, silicates, carbonates and phosphates.

Examples of suitable inorganic builders are aluminosilicates with ion-exchanging properties such as zeolites. Various types of zeolites are suitable, in particular zeolites A, X, B, P, MAP and HS in their Na form or in forms in which Na is partly replaced by other cations such as Li, K, Ca, Mg or ammonium. Suitable zeolites are described, for example, in EP-A 0 038 591, EP-A 0 021 491, EP-A 0 087 035, U.S. Pat. No. 4,604,224, GB-A 2 013 259, EP-A 0 522 726, EP-A 0 384 070 and WO-A 94/24251.

Examples of other suitable inorganic builders are amorphous or crystalline silicates such as amorphous disilicates, crystalline disilicates such as the sheet silicate SKS-6 (manufactured by Hoechst AG). The silicates can be employed in the form of their alkali metal, alkaline earth metal or ammonium salts. Na, Li and Mg silicates are preferably employed.

Further suitable inorganic builders are carbonates and bicarbonates. These can be employed in the form of their alkali metal, alkaline earth metal or ammonium salts. Preferably employed are Na, Li and Mg carbonates and bicarbonates, in particular sodium carbonate and/or sodium bicarbonate.

The inorganic builders may be present in the detergents in amounts of from 0 to 60% by weight together with organic cobuil-ders which are to be used where appropriate. The inorganic builders can be incorporated either alone or in any combination with one another into the detergent. In detergents in powder or granule form, they are added in amounts of from 10 to 60% by weight, preferably in amounts of from 20 to 50% by weight. In structured (multiphase) liquid detergents, inorganic builders are added in amounts of up to 40% by weight, preferably up to 20% by weight. They are suspended in the liquid formulation ingredients.

Detergents in powder or granule form, and liquid detergents contain organic cobuilders in amounts of from 0.1 to 20% by weight, preferably in amounts of from 1 to 15% by weight, together with inorganic builders. The heavy duty detergents in powder or granule form may additionally contain as other conventional ingredients a bleaching system consisting of at least one bleach, where appropriate in combination with a bleach activator and/or a bleach catalyst.

Suitable bleaches are perborates and percarbonates in the form of their alkali metal, in particular their Na, salts. They are present in the formulations in amounts of from 5 to 30% by weight, preferably 10 to 25% by weight. Other suitable bleaches are inorganic and organic peracids in the form of their alkali metal or magnesium salts or partly also in the form of the free acids. Examples of suitable percarboxylic acids and salts thereof are Mg monoterephthalate, phthalimidopercaproic acid and diperdodecanedioic acid. An example of an inorganic peracid salt is potassium peroxomonosulfate (Oxon).

Examples of suitable bleach activators are acylamines such as tetraacetylethylenediamine (TAED), tetraacetylglycoluril, N,N'-diacetyl-N,N'-dimethylurea and 1,5-diacetyl-2,4-dioxohexahydro-1,3,5-triazine, acylated lactams such as acetylcaprolactam, octanoylcaprolactam and benzoylcaprolactam, substituted phenol esters of carboxylic acids such as Na acetoxybenzenesulfonate, Na octanoyloxybenzenesulfonate and Na nonanoyloxybenzenesulfonate, acylated sugars such as pentaacetylglucose, anthranil derivatives such as 2-methylanthranil or 2-phenylanthranil, enol esters such as isopropenyl acetate, oxime esters such as acetone O-acetyloxime, carboxylic anhydrides such as pthhalic anhydride or acetic anhydride.

The bleach activators preferably employed are tetraacetylethylenediamine and Na nonanoyloxybenzenesulfonates. The bleach activators are added to heavy duty detergents in amounts of from 0.1 to 15% by weight, preferably in amounts of from 1.0 to 8.0% by weight, particularly preferably in amounts of from 1.5 to 6.0% by weight.

Suitable bleach catalysts are quaternized imines and sulfone imines as described in U.S. Pat. No. 5,360,568, U.S. Pat. No. 5,360,569 and EP-A 0 453 003, and Mn complexes, cf., for example, WO-A 94/21777. If bleach catalysts are employed in the detergent formulations, they are present therein in amounts of up to 1.5% by weight, preferably up to 0.5% by weight, and in the case of the very active manganese complexes in amounts of up to 0.1% by weight.

The detergents preferably contain an enzyme system. This comprises proteases, lipases, amylases and cellulases normally employed in detergents. The enzyme system may be limited to a single enzyme or comprise a combination of different enzymes. The detergents contain the commercial enzymes as a rule in amounts of from 0.1 to 1.5% by weight, preferably 0.2 to 1.0% by weight, of the formulated enzyme. Examples of suitable proteases are Savinase® and Esperase® (manufactured by Novo Nordisk). An example of a suitable lipase is Lipolase® (manufactured by Novo Nordisk). An example of a suitable cellulose is Celluzym® (manufactured by Novo Nordisk).

The detergents contain as other conventional ingredients preferably soil release polymers and/or antiredeposition agents. These comprise, for example, polyesters from polyethylene oxides with ethylene glycol and/or propylene glycol and aromatic dicarboxylic acids or aromatic and aliphatic dicarboxylic acids, or polyesters from polyethylene oxides with di- and/or polyhydric alcohols and dicarboxylic acids, which are endgroup-capped at one end. Polyesters of these types are known, cf., for example, U.S. Pat. No. 3,557,039, GB-A 1 154 730, EP-A 0 185 427, EP-A 0 241 984, EP-A 0 241 985, EP-A 0 272 033 and U.S. Pat. No. 5,142,020.

Other suitable soil release polymers are amphiphilic graft or other copolymers of vinyl and/or acrylic esters on polyalkylene oxides (cf. U.S. Pat. No. 4,746,456, U.S. Pat. No. 4,846,995, DE-A 3 711 299, U.S. Pat. No. 4,904,408, U.S. Pat. No. 4,846,994 and U.S. Pat. No. 4,849,126) or modified celluloses such as methylcellulose, hydroxypropylcellulose or carboxymethylcellulose.

Antiredeposition agents and soil release polymers are present in the detergent formulations in amounts of from 0 to 2.5% by weight, preferably 0.2 to 1.5% by weight, particularly preferably 0.3 to 1.2% by weight. Soil release polymers which are preferably employed are the graft copolymers, disclosed in U.S. Pat. No. 4,746,456, of vinyl acetate on polyethylene oxide of molecular weight 2500–8000 in the ratio of 1.2:1 to 3.0:1 by weight, and commercial polyethylene terephthalate/polyoxyethylene terephthalates of molecular weight 3000 to 25,000 from polyethylene oxides of molecular weight 750 to 5000 with terephthalic acid and ethylene oxide and a molar ratio of polyethylene terephthalate to polyoxyethylene terephthalate of from 8:1 to 1:1, and the block polycondensates which are disclosed in DE-A 4 403 866 and which contain blocks of (a) ester units from polyalkylene glycols with a molecular weight of 500 to 7500 and aliphatic dicarboxylic acids and/or monohydroxy monocarboxylic acids and (b) ester units from aromatic dicaboxylic acids and polyhydric alcohols. These amphiphilic block copolymers have molecular weights of from 1500 to 25,000.

A typical heavy duty detergent in powder or granule form may have, for example, the following composition:

2–50, preferably 8–30, % by weight of at least one of the anionic and/or nonionic surfactants described above,
5–50, preferably 15–42.5, % by weight of at least one inorganic builder,
5–30, preferably 10–25, % by weight of an inorganic bleach,
0.1–15, preferably 1–8, % by weight of a bleach activator,
0–1, preferably a maximum of 0.5, % by weight of a bleach catalyst,
0.05–5% by weight, preferably 0.2 to 2.5% by weight, of a color transfer inhibitor based on water-soluble homopolymers of N-vinylpyrrolidone or N-vinylimidazole, water-soluble copolymers of N-vinylimidazole and N-vinylpyrrolidone, cross-linked copolymers of N-vinylimidazole and N-vinylpyrrolidone with a particle size of from 0.1 to 500, preferably up to 250 μm, these copolymers containing 0.01 to 5, preferably 0.1 to 2, % by weight of N,N'-divinylethyleneurea as crosslinker; other color transfer inhibitors are water-soluble and cross-linked polymers of 4-vinylpyridine N-oxide obtainable by polymerizing 4-vinylpyridine and subsequently oxidizing the polymers;
0.1–20, preferably 1–15, % by weight of at least one organic cobuilder,
0.2–1.0% by weight of protease,
0.2–1.0% by weight of lipase,
0.3–1.5% by weight of a soil release polymer.

A bleach system is often completely or partly dispensed with in mild specialty detergents (for example in color detergents). A typical color detergent in powder or granule form may have, for example, the following composition:

2–50, preferably 8–30, % by weight of at least one of the anionic and/or nonionic surfactants described above,
10–60, preferably 20–55, % by weight of at least one inorganic builder,
0–15, preferably 0–5, % by weight of an inorganic bleach,
0.05–5% by weight, preferably 0.2–2.5% by weight, of a color transfer inhibitor (cf. above),
0.1–20, preferably 1–15, % by weight of at least one organic cobuilder,
0.2–1.0% by weight of protease,
0.2–1.0% by weight of cellulase,
0.2–1.5% by weight of a soil release polymer, eg. a graft copolymer of vinyl acetate on polyethylene glycol.

The detergents in powder or granule form may contain as other conventional ingredients up to 60% by weight of inorganic fillers. Sodium sulfate is normally used for this purpose. However, the detergents according to the invention preferably have a low filler content of up to 20% by weight, particularly preferably up to 8% by weight of fillers.

The detergents according to the invention may have apparent densities varying in the range from 300 to 950 g/l. Modern compact detergents as a rule have higher apparent densities, eg. 550 to 950 g/l, and a granular structure.

Typical liquid detergents contain, for example:

5–60, preferably 10–40, % by weight of at least one of the anionic and/or nonionic surfactants described above,
0.05–5% by weight, preferably 0.2–2.5% by weight, of a color transfer inhibitor (cf. above),
0.1–20, preferably 1–15, % by weight of at least one cobuilder,
0–1.0% by weight of protease,
0–1.0% by weight of cellulase,
0–1.5% by weight of a soil release polymer and/or antiredeposition agent,
0–60% by weight of water,
0–10% by weight of alcohols, glycols such as ethylene glycol, diethylene glycol or propylene glycol, or glycerol.

The detergents may where appropriate contain further conventional additives. Further additives which may be present are, for example, complexing agents, phosphonates, optical brighteners, dyes, perfume oils, foam suppressants and corrosion inhibitors.

By cleaners are meant, in particular, those for hard surfaces, for example cleaners for metals, plastics, glass and ceramics, floor cleaners, toilet cleaners, all-purpose cleaners for household and commercial applications, industrial cleaners (for use in car washing systems or high-pressure cleaners), low temperature cleaners, dishwashing agents, manual dishwashing agents, rinse aids, disinfecting cleaners, cleaners for the foodstuff and beverage industries, in particular as bottle cleaners, CIP cleaners (cleaning-in-place) in dairies, breweries and other foodstuff manufacturing plants.

Besides said applications in textile laundering and as cleaners for hard surfaces, there are also suitable applications in cosmetics, in the photographic industry, in crop protection formulations and in chain lubricants.

Further possible areas of application of the novel fatty amide derivatives XV are the following:

Surfactants for Domestic Products:

Besides said detergents, they can also be used in laundry aids such as detergency boosters for heavy, localized fatty soiling, and presoakers generally for heavily soiled laundry. Detergency boosters are products formulated with a high surfactant content and mainly used for easy-care textiles for which certain washing temperatures must not be exceeded. Presoakers are usually laundry aids with a highly alkaline formulation based on mixtures of anionic and nonionic surfactants which loosen tenacious and firmly adherent soil.

After-treatment compositions (after the actual washing process) such as fabric softeners, tumbler aids, fabric formers, spray starches, ironing auxiliaries and other stiffeners.

Carpet cleaners, including spot removers which are available inter alia as aerosols to remove water-soluble spots based on surfactant and alcohol, and foam cleaners (spray and liquid products with aqueous solutions of surfactants to which water-soluble organic solvents may be added), and powder cleaners and spray extraction cleaners. The powder cleaners suitable for intermediate cleaning consist of a combination of solutions of active substances with cleaning activity and carrier materials with a large surface area. The active substances comprise mixtures of surfactants, solvents and water. Spray extraction cleaners are concentrated aqueous solutions or powders which comprise surfactants and water softeners, with or without antifoam agents.

Besides dishwashing agents (manual and machine), also suitable are cleaners such as all-purpose cleaners, scouring agents and specialty cleaners (eg. for scale in kettles and toilet bowls).

Surfactants for Industrial Cleaners:

In this connection, mention should be made of solvent-containing cleaners and aqueous cleaners (alkaline, neutral, acidic), surfactants for washing cars, trucks and railway carriages (automatic washing lines and systems and automobile washes, and for manual automobile cleaning), passivating cleaners (cleaners passivate iron surfaces when they dry out on them) and combined cleaners and disinfectants (food-processing industry).

Other Surfactants in the Foodstuff Industry:

Promoting and/or stabilizing oil-in-water emulsions (mayonnaise, sauces, etc.) and water-in-oil emulsions (margarine and the like), also in the manufacture and processing of (soft) ices, biscuits, chewing gum, liquorice, caramels, chocolate, bakery products, dry products (such as drinks powders, powdered milk, blancmange powder, etc.), sausages and cheese.

Surfactants in Agriculture:

Besides crop protection formulations, they are also suitable for fertilizers, artificial fertilizers and salts (powders, granules, prills) which are prone to form agglomerates ("caking"). Anticaking properties are shown by surfactants when they form a hydrophobic film on the surface of the crystals and displace the water.

Surfactants in the Pharmaceutical Industry (and in disinfectants):

Thus, for example, the active ingredient in a formulation can be specifically activated by surfactants to control absorption and tolerability.

Surfactants in the Production of Synthetic Fibers and in the Textile Industry:

Pretreatment of fibers, manufacture of rayon fibers, spinning preparations and textile lubricants, dyeing assistants, finishing agents, water repellants, assistants for printing, antistatics and flocking and coating agents may be mentioned in this connection.

Surfactants in the Plastics Industry:

Suitable in this connection are the production of synthetic dispersions, bead polymers, foams, microcapsules and use in surface-active mold release agents, for coloring plastics and for antistatic finishing of plastics.

Surfactants for Biotechnology and for Paints, Pigments and Printing Inks

Surfactants for Cosmetic Care Articles and Cosmetic Cleaners

Surfactants in the Pulp and Paper Industry:

They are suitable for removing resin in the production of pulp and paper manufacture, pigment dispersing and foam control in the manufacture of paper and paper coatings, paper sizes and their dispersion or emulsion in paper finishing, for cleaning the machinery, for straining and felting, for the regeneration/deinking of waste paper, for recovering fibers and wet strengthening.

Surfactants in Adhesives

Surfactants in the Leather Industry:

In this connection they are used for pretreatment of the leather, tanning of the leather, after-treatment of the wet (eg. fatliquoring) and dry leather (eg. finishing) and care of the leather. Said surfactants XV are furthermore suitable as dye penetration aids in leather dyeing.

Surfactants in the Photographic Industry:

In this connection, mention should be made of coating agents, antistatics, lubricants, emulsifiers and dispersants for producing active substance emulsions, dispersions and latices and additives to processing baths.

Surfactants in the Metal-Processing Industry:

They are suitable in and for producing cooling lubricants, hardening oils, hydraulic oil emulsions, polishing pastes, mold release agents, drawing oils, pickling agents, metal cleaners and metal driers.

Surfactants in Electoplating

Surfactants in Corrosion Inhibition

Surfactants for the production of polishes and protective layers and for their removal, especially in compositions for care of floors, shoe polishes, furniture, automotive paints and other items used in the household and in industry.

Surfactants as Additives in the Mineral Oil Industry:
Additives for fuels (Otto and diesel engines), aircraft turbines, heating oils and lubricants are of interest in this connection.
Surfactants for Road Building, for Building Materials and Soil Remediation
Surfactants in Mining and in Flotation
Surfactants for the Production and Processing of Petroleum:
In this connection they are used for extraction of petroleum, for emulsion breaking, as wetting agents, in drill flushing, as corrosion inhibitors, for removing oil spills, for improving infectivity in water flooding, as paraffin inhibitors.

Surfactants as biocides, in controlling fires (foam fire extinguishers, rapid wetting of parts of buildings); treatment of glass apparatus and glass fibers in order to retain their strength and the required properties; to control dust (eg. surfactants are added to the spray water used in grinding processes); surfactants for pumping fine coal dust or non-flowing heavy oils with the aid of aqueous dispersions (slurries) through pipelines (burning).

Cleaners containing the surfactants XV according to the invention are particularly suitable for cleaning hard surfaces such as glass, ceramic, plastic and metal, eg. floors and wall and floor tiles. The cleaners can be adjusted to be alkaline, acidic or neutral. They normally contain surfactants in amounts of about 5 to 90, preferably 10 to 75, % by weight based on the active substance content. They may be anionic, nonionic or cationic surfactants or mixtures of surfactants which are compatible with one another, eg. mixtures of anionic and nonionic or of cationic and nonionic surfactants. Alkaline cleaners may contain sodium carbonate, potassium carbonate, sodium bicarbonate, potassium bicarbonate, sodium sesquicarbonate, potassium sesquicarbonate, sodium hydroxide, potassium hydroxide, amine bases such as monoethanol-amine, diethanolamine, triethanolamine, ammonia or silicate in amounts of up to 60% by weight, and in some cases even up to 80% by weight. The cleaners may additionally contain citrates, gluconates or tartrates in amounts of up to 80% by weight. They may be in solid or in liquid form.

The fatty amide derivatives XV according to the invention are particularly advantageous because they
- have an excellent profile of use properties as surfactants in detergents and cleaners, particular mention being made in this connection of the universal fat-dissolving capacity, the good single wash cycle performance and the good wetting capacity;
- are low-foam and readily biodegradable;
- have a low surface tension and very low interfacial tension;
- show synergistic effects in combination with nonionic surfactants and, in some cases, with anionic surfactants;
- have good solubility even in hard water and are insensitive to water hardness;
- can in many cases be produced free of solvent or dispersant;
- can be produced in simple apparatus at low cost and in high yields with short reaction times;
- can be produced by reactions whose progress can be followed quickly and easily, for example by infrared spectroscopy (IR), gas chromatography (GC) or by conventional titration methods.

It has emerged in many cases that mixtures of
(i) fatty amide derivatives of the general formula XVIII

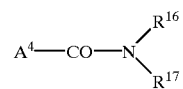

(XVIII)

in which the substituents have the following meanings:
$A^4$ an aliphatic $C_8$–$C_{24}$ radical with unbranched carbon chain, which chain contains one or more groups of the formula XVI

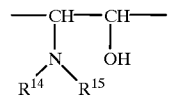

(XVI)

$R^{14}$ and $R^{16}$, independently of one another, a hydroxyl- and/or amino-substituted hydrophilic radical having 2 to 40 carbon atoms or a $C_1$–$C_{14}$-alkyl radical which has carboxyl and/or sulfo groups in the form of the free acids and/or their alkali metal or ammonium salts and which may be interrupted by nonadjacent oxygen atoms, —NH groups and/or N-$C_1$–$C_4$-alkyl groups, and
$R^{15}$ and $R^{17}$ hydrogen, an unsubstituted $C_1$–$C_6$-alkyl radical or a radical $R^{14}$ or $R^{16}$, and (ii) fatty amide derivatives of the general formula XIX

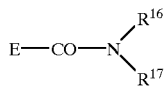

(XIX)

where
E is an aliphatic $C_8$–$C_{24}$ radical with unbranched carbon chain, which chain contains one or more groups of the formula XX

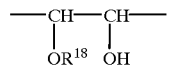

(XX)

where
$R^{18}$ is $C_1$–$C_4$-alkyl, and
$R^{16}$ and $R^{17}$ have the abovementioned meanings, where the ratio by weight of components (i) and (ii) is from 99:1 to 1:99, in particular 90:10 to 30:70, especially 80:20 to 45:55, lead to improvements in the physico-chemical and use data on use as surfactants in detergents and cleaners. The present invention therefore also relates to these mixtures.

Mixtures of particular interest in this connection are those in which the abovementioned fatty amide derivatives XV (ie. $R^{16}/R^{17}=R^{12}/R^{13}$) occur as component (i).

Suitable as radical $R^{18}$ are, in particular, ethyl, propyl, isopropyl, butyl, tert-butyl and, especially, methyl.

Mixtures according to the invention of components (i) and (ii) may be, for example:
Mixtures of fatty amide derivatives XVIII in which the groups —N($R^{14}$)$R^{15}$ and —N($R^{16}$)$R^{17}$ are each derived from hydroxyalkylamines or aminoalkylamines (—N($R^{14}$)$R^{15}$ and —N($R^{16}$)$R^{17}$ are preferably identical), and fatty amide derivatives XIX which are likewise based on hydroxyalkylamines or aminoalkylamines in the amide group (the amines preferably identical to the amines in XVIII);

Mixtures of fatty amide derivatives XVIII in which the groups —N($R^{14}$)$R^{15}$ and —N($R^{16}$)$R^{17}$ are each derived from amino acids (—N($R^{14}$)$R^{15}$ and —N($R^{16}$)$R^{17}$ are preferably identical), and fatty amide derivatives XIX which are likewise based on amino acids in the amide group (the amino acids preferably identical to the amino acids in XVIII);

Mixtures of fatty amide derivatives XVIII in which the groups —N($R^{14}$)$R^{15}$ are derived from amino acids and the group —N($R^{16}$)$R^{17}$ is derived from hydroxyalkylamines or aminoalkylamines, and fatty amide derivatives XIX which are likewise based on hydroxyalkylamines or aminoalkylamines in the amide group (the amines preferably identical to the amines in the amide group —N($R^{16}$)$R^{17}$ of XVIII);

Mixtures of fatty amide derivatives XVIII in which the groups —N($R^{14}$)$R^{15}$ are derived from hydroxyalkylamines or aminoalkylamines and the group —N($R^{16}$)$R^{17}$ is derived from amino acids, and fatty amide derivatives XIX which are likewise based on amino acids in the amide group (the amino acids preferably identical to the amino acids in the amide group —N($R^{16}$)$R^{17}$ of XVIII).

The mixtures according to the invention can be produced by reacting appropriate epoxidized fatty amides, in particular the abovementioned epoxidized fatty amides XVII, or appropriate epoxidized fatty acid esters, fatty acids or their salts with appropriate amines in the presence of alkanols of the formula $R^{18}$—OH or their salts. Some of the epoxy groups then react with the amine, and the others react with the alkanol. The resulting fatty amide derivatives XIX are, just like the fatty amide derivatives XVIII, usually mixtures of isomers because the oxirane rings can open at both C—O bonds.

Since the reaction of said epoxidized fatty acid derivatives with the amines takes place in some cases with catalysis by alkali metal alcoholate (for example, for this purpose preferably 1 to 60 mol %, in particular 5 to 30 mol %, based on amine to be reacted, of an alkali metal alcoholate such as sodium methanolate or sodium ethanolate are added), the incorporated radical —$OR^{18}$ originates from this alcoholate. If a fatty acid lower alkyl ester, eg. a fatty acid methyl ester, is used as starting material, the incorporated radical —$OR^{18}$ originates from this alcohol which is liberated by exchange of the alcohol residue by the amine residue.

Besides more beneficial physicochemical and use properties, the mixtures according to the invention also have the advantage that it is no longer necessary to remove excess amide to prepare them if this free amine is unwanted in the product because, without the reaction with alkanols $R^{18}$—OH, normally excess amounts of amine are required in order completely to open the oxirane ring, since amines are somewhat less reactive with oxiranes than are alcohols or alcoholate ions under the reaction conditions. In addition, the mixtures according to the invention are readily biodegradable.

The present invention furthermore relates to detergents and cleaners which comprise the mixture according to the invention of components (i) and (ii) as surfactants in amounts conventional for this purpose, and other additives conventional for such compositions. Said surfactant mixture of (i) and (ii) is furthermore suitable as dye penetration aid in leather dyeing.

The present invention is illustrated in detail by the following examples.

The percentage data in the examples mean % by weight unless otherwise evident therefrom.

Example 15
Product of the Reaction of Diethanolamine and Sarcosine with Epoxidized Rapeseed Oil Methyl Ester 52.5 g (0.5 mol) of diethanolamine were added at 100° C. to 152.8 g (0.5 mol) of epoxidized rapeseed oil methyl ester and 14.4 g of $NaOCH_3$ (30% strength in methanol, 0.08 mol). After the addition was complete, the mixture was stirred for 15 min and checked by IR and GC for complete amidation, and then 56.0 g (0.5 mol) of sarcosine sodium salt were added, and the mixture was heated at 160° C. for 6 h. Conversion was checked by GC, amine/epoxide double titration and the Preußmann test and, after the reaction was complete, the product mixture was discharged. The product was a yellowish brown solid and gave a clear solution in water.

Example 16
Product of the Reaction of Diethanolamine and Glycine with Epoxidized Rapeseed Oil Methyl Ester 52.5 g (0.5 mol) of diethanolamine were added at 100° C. to 152.8 g (0.5 mol) of epoxidized rapeseed oil methyl ester and 14.4 g of $NaOCH_3$ (30% strength in methanol, 0.08 mol). After the addition was complete, the mixture was stirred for 15 min and checked by IR and GC for complete amidation, and then 49.1 g (0.5 mol) of glycine sodium salt were added, and the mixture was heated at 150° C. for 6 h. Conversion was checked by GC, amine/epoxide double titration and the Preußmann test and, after the reaction was complete, the product mixture was discharged. The product was a pale yellow solid and gave a clear solution in water.

Example 17
Product of the Reaction of Aminopropyldiethanolamine and Glycine with Epoxidized Rapeseed Oil Methyl Ester 81.2 g (0.5 mol) of aminopropyldiethanolamine were added at 100° C. to 152.8 g (0.5 mol) of epoxidized rapeseed oil methyl ester and 14.4 g of $NaOCH_3$ (30% strength in methanol, 0.08 mol). After the addition was complete, the mixture was stirred for 20 min and checked by IR and GC for complete amidation, and then 49.1 g (0.5 mol) of glycine sodium salt were added, and the mixture was heated at 150° C. for 6 h. Conversion was checked by GC, amine/epoxide double titration and the Preußmann test and, after the reaction was complete, the product mixture was discharged. The product was a pale yellow solid and gave a clear solution in water.

Example 18
Product of the Reaction of Aminopropyldiethanolamine and Sarcosine with Epoxidized Rapeseed Oil Methyl Ester 41.8 g (0.26 mol) of aminopropyldiethanolamine and 7.4 g (0.04 mol, 33% strength in methanol) of $NaOCH_3$ were introduced into a laboratory reactor under protective gas.

Then 89.0 g (0.3 mol) of epoxidized rapeseed oil methyl ester were added dropwise. During this, the mixture was heated to 120° C. After 20 min, intermediate III had already formed and was easily detectable by GC analysis. The methanol liberated from the methyl ester remained (just like the methanol from the 30% strength $NaOCH_3$ solution) in the reaction vessel (reflux). 78.4 g (0.3 mol) of sarcosine sodium salt solution (aqueous, 42.9% strength) were added to this mixture with stirring. 15 g of water were also added to dilute. After the addition was complete, the temperature was raised to 140° C. The mixture was then stirred for about 10 h until epoxide (intermediate XVI) was no longer detectable by GC. The reaction product was discharged. The surfactant was obtained as a dark yellow oil.

Use properties

The use properties of the fatty amide derivatives XV investigated were the interfacial tension, the contact angle, the surface tension, the solubility and the fat-removal capacity. The results of the measurements on the substances of Examples 15 and 16 are compiled in Table 8.

The interfacial tension was determined as a function of the time of contact between aqueous surfactant solution and an oil phase.

The contact angle was measured as the wettability of a hard surface by the surfactant solution. In this case, complete wetting (spreading) corresponds to a contact angle of zero.

The surface tension was determined by the DIN 53914 method, by measuring the force in mN/m necessary to pull a plate or a horizontally suspended ring out of the liquid surface.

To determine the fat-removal capacity, small solid plates covered with engine oil or neutral oil are immersed horizontally in the surfactant solution (c=1 g/l) to be investigated. The time until the first oil drop is removed from the particular plate is measured. A shorter time means a better fat-removal capacity.

TABLE 8

| Sample | Example 15 | | Example 16 | | for comparison: LAS | |
|---|---|---|---|---|---|---|
| pH | 10.0 | | 10.3 | | | |
| Consistency | yellowish brown, solid | | yellow, solid | | | |
| Interfacial tension [mN/m] (1 g/l; 25° C.) | 1 min | 30 min | 1 min | 30 min | 1 min | 30 min |
| Olive oil | 1.0 | 0.28 | 0.87 | 0.20 | 0.56 | 0.53 |
| Neutral oil | 0.54 | 0.63 | 0.60 | 0.63 | 1.3 | 1.2 |
| Contact angle [degrees] (0.2 g/l; 40° C.) $H_2O$ | | | | | | |
| Polyethylene | 110 | | 0 | | 0 | 78 |
| Stainless steel | 76 | | 0 | | 0 | 60 |
| Ceramic | 83 | | 29 | | 0 | 55 |
| Glass | 77 | | 37 | | 33 | 32 |
| Surface tension [mN/m] | 0.2 g/l | 1 g/l | 0.2 g/l | 1 g/l | 0.2 g/l | 1 g/l |
| 25° C. | 38.7 | 38.0 | 38.2 | 38.0 | | 36.1 |
| 40° C. | 35.8 | 34.7 | 35.3 | 36.0 | 46.0 | 34.7 |

TABLE 8-continued

| Sample | Example 15 | Example 16 | for comparison: LAS |
|---|---|---|---|
| Solubility [1 g/l] (Turbidity units) Deionized water | | | |
| 25° C. | 0.3 (clear) | 0.1 (clear) | 1 (clear) |
| 40° C. | 0.2 (clear) | 0.1 (clear) | 1 (clear) |
| Water 20° hardness 25° C. | 780 (cloudy) | 370 (cloudy) | flocculates |
| Fat-removal capacity [sec] (1 g/l; 40° C.) (Olive oil/ neutral oil) | | | |
| Stainless steel | >600/>600 | >600/>600 | >600/>600 |
| Ceramic | >600/>600 | >600/>600 | >600/>600 |
| Glass | 127/9 | 18/30 | 360/65 |

LAS: Na dodecylbenzenesulfonate

The fatty amide derivatives XV according to the invention show a property profile typical of anionic surfactants. They are superior to conventional anionic surfactants such as LAS due to a lower surface tension and lower interfacial tension, especially on lengthy contact with oil. They show, in particular, a very good fat-removal capacity for olive oil and neutral oil on glass, and, as a rule, they give a clear solution in water or only a little cloudiness in hard water.

Good use properties similar to those for the products of the reaction of diethanolamine with sarcosine or glycine and epoxidized rapeseed oil methyl ester (Example 15 or 16) are shown by the products of the reaction of aminopropyldiethanolamine with sarcosine or glycine and epoxidized rapeseed oil methyl ester (Example 17 or 18).

Example 19 and Comparative Example 20

The substances from Example 15 were additionally tested under standard conditions (60° C., 5 g/l) in a model detergent formulation together with a $C_{13/15}$ oxo alcohol reacted with 7 mol of ethylene oxide as nonionic surfactant (19% surfactant added, of which 47% is the substance from Example 15 and 53% is said nonionic surfactant) (Example 19). A similar model detergent formulation with 19% surfactant added, of which 47% was a $C_{12/18}$-alkyl sulfate as anionic surfactant and 53% of said nonionic surfactant, was used for comparison (Example 20).

The washing tests were carried out under the following conditions:

| | |
|---|---|
| Washing machine | Atlas Launder-O-meter |
| Wash cycles | 1 |
| Rinse cycles | 1 |
| Washing temperature | 60° C. |
| Washing time | 30 min |
| Water hardness | 3 mmol/l |
| Ca:Mg | 4:1 |
| Amount of liquor | 250 ml |

-continued

| | |
|---|---|
| Detergent concentration | 5 g/l |
| Soiled fabric | WFK 10 D, WFK 20 D Test fabric from WfK-Test-gewebe GmbH EMPA 101, EMPA 104 Test fabric from the Eidgenössische Materialprüfanstalt St. Gallen |
| Detergent formulation A: | |
| Zeolite A | 30% |
| Sodium carbonate | 12% |
| Sodium silicate | 3% |
| Tylose CR 1500 p | 1.2% |
| Sodium perborate monohydrate | 14.4% |
| Tetraacetylethylenediamine | 4% |
| Acrylic acid/maleic acid copolymer (MW 70000) | 5% |
| Soap | 0.5% |
| Sodium sulfate | 4% |
| Water | 6.9% |
| Surfactant mixture (see above) | 19% |

Rinsing was followed by spinning, and the fabrics were hung up individually to dry. The fabric was measured with an Elrepho 2000 from Data Color, Heidenheim, specifically 6 points being measured on each piece of fabric. The reflectance was determined at 480 nm.

The total reflectance R for Example 19 was 205.9 ($\hat{=}$82.1 absolute efficiency) and for Comparative Example 20 was 190.7 ($\hat{=}$75.9 absolute efficiency) (blank without surfactant system: R=140.6$\hat{=}$41.6 absolute efficiency). It is clear from this that the combination of the fatty amide derivatives XV according to the invention with nonionic surfactants yields synergistic effects in the single wash cycle performance.

Examples 21 to 23
Products of the Reaction of Diethanolamine with Epoxidized Rapeseed Oil Methyl Ester in the Presence of Sodium Methoxide/Methanol (Example 21)

A mixture of 1575 g (15 mol) of diethanolamine and 369 g of sodium methoxide solution (2.0 mol, 30% strength in methanol) was heated under a protective gas atmosphere and under reflux to 90° C. and, at this temperature, 2291 g (7.5 mol) of epoxidized rapeseed oil methyl ester were slowly added. The mixture was subsequently heated to 130° C. and then stirred at this temperature for 5 h. Conversion was checked by GC, amine/epoxide double titration and the Preußmann test and, after the reaction was complete, the product mixture was discharged. The reaction product was obtained as a highly viscous yellowish liquid. It contained the corresponding components (i) and (ii) in the ratio of 80:20 by weight.

Example 22

Example 21 was repeated with the difference that only 7.5 mol of diethanolamine were employed in place of 15 mol of diethanolamine. The resulting product mixture contained the corresponding components (i) and (ii) in the ratio of 45:55 by weight.

Example 23

A product mixture was produced in a similar manner to Example 21 starting from 15 mol of diethanolamine, 2.0 mol of NaOCH$_3$, 15 mol of methanol and 7.5 mol of epoxidized rapeseed oil methyl ester and contained the corresponding components (i) and (ii) in the ratio of 61:39 by weight.

Use Properties

The use properties investigated for the mixtures of components (i) and (ii) were the interfacial tension, the contact angle, the surface tension, the cloud point, the wetting capacity on cotton, the solubility and the fat-removal capacity. The results of the measurements on the mixtures of products of Examples 21 to 23 are summarized in Table 9.

The interfacial tension was determined as a function of the time of contact between aqueous surfactant solution and an oil phase.

The contact angle was measured as the wettability of a hard surface by the surfactant solution. In this case, complete wetting (spreading) corresponds to a contact angle of zero.

The surface tension was determined by the DIN 53914 method, by measuring the force in mN/m necessary to pull a plate or a horizontally suspended ring out of the liquid surface.

The cloud point was determined by the DIN 53917 method. This entails measurement of the temperature above which the solution becomes cloudy and thus exists as a mixture of two liquid phases. A lower cloud point generally means a lower foam capacity.

To determine the fat-removal capacity, small solid plates covered with neutral oil or olive oil are immersed horizontally in the surfactant solution (c=1 g/l) to be investigated. The time until the first oil drop is removed from the particular plate is measured. A shorter time means a better fat-removal capacity.

TABLE 9

| Sample | Example 21 | | Example 22 | | Example 23 | |
|---|---|---|---|---|---|---|
| Consistency, 100% in each case | brown, highly viscous | | brown, highly viscous | | yellowish brown, viscous | |
| pH (1 g/l) | 10.2 | | 10.3 | | 10.4 | |
| Interfacial tension [mN/m] (1 g/l; 25° C.) | 1 min | 30 min | 1 min | 30 min | 1 min | 30 min |
| Decane | 1.1 | 0.26 | 0.10 | 0.11 | 0.11 | 0.26 |
| Olive oil | 1.3 | 0.34 | 2.7 | 0.49 | 0.05 | 0.21 |
| Neutral oil | 0.15 | 0.10 | 0.18 | 0.18 | | |
| Hexadecane | 0.35 | 0.13 | 0.10 | 0.06 | | |
| Contact angle [degrees] (0.2 g/l; 40° C.) H$_2$O | | | | | | |
| Polyethylene 110 | 0 | | 0 | | | |
| Stainless steel 76 | 0 | | 0 | | | |
| Ceramic 83 | 0 | | 0 | | | |
| Glass 77 | 38 | | 0 | | | |
| Surface tension [mN/m] | 0.2 g/l | 1 g/l | 0.2 g/l | 1 g/l | 0.2 g/l | 1 g/l |
| 25° C. | 32.9 | 32.2 | 30.5 | 30.7 | 33.0 | 3.2 |
| 40° C. | 32.1 | 31.3 | 29.3 | 29.0 | 31.9 | 32.0 |
| Cloud point in water [° C.] 10 g/l | >100 | | cloudy at 20° C. | | | |
| Solubility [1 g/l] (turbidity units) | | | | | | |

TABLE 9-continued

| Sample | Example 21 | Example 22 | Example 23 |
|---|---|---|---|
| Deionized water | | | |
| 25° C. | 1 (clear) | 24 (slightly cloudy) | 4 (clear) |
| 40° C. | 1 (clear) | 24 (slightly cloudy) | 62 (slightly cloudy) |
| Water at 20° hardness 25° C. | 1200 (very cloudy) | 350 (very cloudy) | 825 (very cloudy) |
| Fat-removal capacities [sec] (1 g/l; 40° C.) (Olive oil/ neutral oil) | | | |
| Teflon | 400/22 | >600/4 | |
| Polyethylene | >600/>600 | >600/>600 | |
| Stainless steel | >600/>600 | >600/>480 | |
| Ceramic | 125/440 | >600/>410 | |
| Glass3 | 210/9 | >600/>125 | |

The interfacial tensions of the mixtures according to the invention of components (i) and (ii) with respect to the various oils are distinctly less than with conventional nonionic surfactants such as appropriate sugar surfactants or appropriate fatty alcohol ethoxylates. The wetting capacity on cotton of the mixtures according to the invention is at least as good as for most conventional nonionic surfactants. Their fat-removal capacity on various surfaces is distinctly better, especially for olive oil, than with many conventional nonionic surfactants, for example fatty alcohol ethoxylates.

Biodegradability

The mixtures according to the invention of components (i) and (ii) show in the modified Sturm test degradations of the order of 40 to 60% DOC removal after 28 days and in the Zahn-Wellens test degradations of the order of 50 to 70% after 28 days, and 80 to 90% after 56 days (DOC elimination in each case). As the content of component (ii) in the mixtures according to the invention increases there is also a marked increase in the biodegradability.

However, it has emerged not only that the mixtures defined above of fatty amide derivatives XVIII and fatty amide derivatives XIX are of interest, but also that the pure fatty amides with vicinal alkoxy/hydroxy substitution or vicinal dihydroxy substitution in the fatty acid chain often has improved physicochemical and use data as surface-active substances.

K. L. Johnson describes in J. Am. Oil Chem. Soc. 43 (1966) 497–500 the compounds obtainable by reacting methylpolyglycols with methyl epoxy stearate and subsequent reaction with alkanolamines as nonionic detergents based on epoxidized oils. The reaction of the methylpolyglycols with the epoxy ester takes place in the presence of a Friedel-Crafts catalyst such as tin tetrachloride, boron trifluoride or antimony pentachloride. The resulting fatty amides are recommended as surface-active agents in low-foam cleaners, in dishwashing agents, in floor cleaners and in other cleaning formulations.

WO-A 90/09366 discloses fatty amides with vicinal $C_3$–$C_{10}$-alkenyloxy (or alkynyloxy)-hydroxy substitution in the fatty acid chain. These are suitable as emulsifiers, textile assistants or cosmetic additives.

Since there has been no description in the prior art of fatty amides with corresponding vicinal $C_1$–$C_4$-alkoxy/hydroxy substitution, and they have proven advantageous, the present invention also relates to fatty amide derivatives of the general formula XXI

(XXI)

where

G is an aliphatic $C_8$–$C_{24}$ radical with unbranched carbon chain, which chain contains one or more groups of the formula XXII

(XXII)

where $R^{19}$ is $C_1$–$C_4$-alkyl or hydrogen, $R^{16}$ is a hydroxyl- and/or amino-substituted hydrophilic radical having 2 to 40 carbon atoms or a $C_1$–$C_{14}$-alkyl radical which has carboxyl and/or sulfo groups in the form of the free acids and/or their alkali metal or ammonium salts and which may be interrupted by nonadjacent oxygen atoms, —NH groups and/or N-$C_1$–$C_4$-alkyl groups, and $R^{17}$ is hydrogen, an unsubstituted $C_1$–$C_6$-alkyl radical or a radical $R^{16}$.

Suitable unsaturated unbranched aliphatic fatty acids are those mentioned above. Unsaturated $C_{18}$ fatty acids are preferred.

A particularly suitable $C_1$–$C_4$-alkyl radical for $R^{19}$ is methyl.

The amines $HN(R^{16})R^{17}$ which underlie the amide groups in XXI and have one or two nonionic hydrophilic substituents may be branched and have several hydroxyl or amino groups, such as tris(hydroxymethyl)methylamine, but preferably have at least one unbranched ω-hydroxyalkyl group or one unbranched ω-aminoalkyl group having, in each case, 2 to 6 carbon atoms, it being possible for the underlying alkyl group to be interrupted by nonadjacent oxygen atoms, NH groups, N-$C_1$–$C_4$-alkyl groups, N-$C_1$–$C_4$-hydroxyalkyl groups or N-$C_1$–$C_4$-aminoalkyl groups. Also suitable are N-$C_1$–$C_4$-alkyl-substituted derivatives if they also contain at least one reactive amino or imino group.

Particularly suitable amines of these types are those mentioned above.

The compounds containing carboxyl and/or sulfo radicals and underlying the amide groups —$N(R^{16})R^{17}$ in XXI are, in particular, amino acids as mentioned above.

The present invention also relates to a process for preparing the fatty acid derivatives XXI according to the invention, which comprises reacting an epoxidized fatty acid derivative of the formula XXIII

(XXIII)

where $B^3$ is an aliphatic $C_8$–$C_{24}$ radical with unbranched carbon chain, which chain contains one or more epoxy groups, and R²⁰ is a hydroxyl radical and its alkali metal or ammonium salts, a $C_1$–$C_4$-alkoxy radical or a radical of a mono-, di- or triglyceride, where the di- or triglyceride radicals are radicals of natural saturated or unsaturated fatty acids, with a $C_1$–$C_4$-alkanol or water with catalysis by protonic acids or Lewis acids to give a fatty acid derivative of the formula XXIV $$G\text{—}CO\text{—}R^{20} \tag{XXIV}$$

where G has the abovementioned meaning, and subsequently converting with an amine of the formula XXV

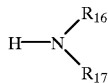
(XXV)

into the fatty amide derivative XXI.

Reaction of the epoxidized fatty acid derivative with 2 equivalents of amine takes place with base catalysis in the conventional process as described above. One mole equivalent of the amine reacts with the ester first to form an amide, and then the remaining amine reacts with the epoxide. The alkanol liberated from the alkyl ester, just like the alkanol from the alcoholate catalyst solution, usually remains in the reaction system in this process, which means that the alcohol competes with the amine to attack the epoxy group and there is also formation of structures with alkoxy substitution in the fatty acid chain.

In the process according to the invention there is first acid-catalyzed, preferably with Lewis acids such as $BF_3$, $OEt_2$, $FeCl_3$ or $TiCl_4$ or with protonic acids such as tetrafluoroboric acid, ortho-phosphoric acid or phosphorous acid or with acidic ion exchanger, reaction of the epoxidized fatty acid derivative XXIII, usually an ester or triglyceride, with the alcohol. This entails very rapid opening of the epoxide to give the vicinal alkoxy/hydroxy fatty acid ester. No transesterification takes place. This ester or this triglyceride is then reacted with the hydrophilic amine or amino acid with base catalysis to give the surface-active compound. The vicinal alkoxy/hydroxy fatty acid ester can be purified by distillation or else employed directly in the subsequent amidation. These two reaction steps can also be combined without difficulty into a one-pot reaction. It is necessary in this case to employ slightly more basic catalyst to neutralize the acidic catalyst.

It is likewise possible by this novel process to react the epoxidized fatty acid derivative, usually an ester or triglyceride, with acid catalysis, preferably with protonic acids such as $H_3PO_4$, $H_3PO_3$ or $HBF_4$ or with acidic ion exchanger, with water. This entails opening of the epoxide to give the vicinal dihydroxy fatty acid ester. Virtually no hydrolysis to the carboxylic acid takes place under the selected reaction conditions. This ester is subsequently reacted with the hydrophilic amine or the amino acid. The vicinal dihydroxy fatty acid ester can be purified by distillation or else employed directly in the subsequent amidation.

The process according to the invention differs from the conventional base-catalyzed process in particular in that the overall reaction time is distinctly reduced because the rate-determining epoxide opening is considerably faster with the present acid catalysis (as a rule <30 min compared with >300 min).

Since, as described above, two equivalents of amine are employed per epoxidized fatty acid derivative in the conventional process, normally a residue of unreacted amine remains in the product due to byproduct formation (up to 20% by weight possible depending on conditions). In the acid-catalyzed process, the amine is required exclusively for amidating the ester. Competing reactions are negligible. Thus the amine is virtually completely reacted. It is therefore possible with this process to achieve a residual amine content in the product of <1% by weight.

The uniform products prepared by the acid-catalyzed process have high viscosity and sufficient purity and all form clear solutions in water.

The amidation can be carried out without solvent. However, opening of the epoxide with the alcohol normally requires a certain excess of alcohol (usually 5 to 10 equivalents of alcohol) as solvent. The excess alcohol can subsequently be removed from the product without difficulty, for example by distillation. The alcohol can be reused for opening the epoxide. Toluene or cyclohexane is preferably added in the synthesis of the vicinal dihydroxy fatty acid esters. It is possible in both cases for the solvent subsequently to be removed easily from the higher-boiling required product under reduced pressure. However, direct reaction of the epoxidized oil in water is also possible (without additional organic solvent). Addition of a phase-transfer catalyst in this case reduces the reaction time.

The fatty amide derivatives XXI according to the invention are compounds with excellent surface-active properties and are thus outstandingly suitable for use as nonionic or anionic surfactants in detergents and cleaners as described above. Low surface and interfacial tensions are found in tests. In addition, they show a good fat-dissolving capacity and a good single wash cycle performance. They moreover show good solubility even in hard water, and generally an insensitivity to water hardness.

The present invention therefore also relates to detergents and cleaners which comprise the fatty amide derivatives XXI according to the invention as surfactants in the amounts customary for this purpose, and other additives customary for compositions of this type. Said surfactants XXI are also suitable as dye penetration aids in leather dyeing.

The fatty amide derivatives XXI according to the invention can be prepared straightforwardly and at low cost by the described process. If the reaction is carried out as the one-pot reaction mentioned, only a single apparatus (eg. a conventional stirred vessel) is required, and the reaction can be carried out therein with short reaction times and high yields. In this case the progress of the reaction can be followed rapidly and simply for example by infrared spectroscopy, gas chromatography (GC) or titrations.

The fatty amide derivatives XXI according to the invention are based on renewable raw materials and are therefore particularly advantageous ecologically. As a rule, they are readily biodegradable.

The present invention is illustrated in detail by the following examples.

The percentage data in the examples mean % by weight unless otherwise evident therefrom.

Example 24
Synthesis of Methyl 9(10)-hydroxy-10(9)-methoxystearate by Reaction of Epoxidized Rapeseed Oil Methyl Ester with Methanol 4461 g (15.04 mol) of epoxidized rapeseed oil methyl ester were added to 3000 g (93.75 mol) of methanol. Then, at room temperature, a total of 12.4 g (0.087 mol) of $BF_3 \cdot OEt_2$ were slowly added dropwise, during which the reaction mixture started to boil. Stirring was continued for 30 min without further heating, the completeness of conversion was checked by GC analysis, and then 4.7 g (0.26 mol) of $H_2O$ were added to hydrolyze the $BF_3 \cdot OEt_2$. The mixture was then concentrated under reduced pressure (45° C.). The resulting ester could be used directly for further reactions.

Example 25
Synthesis of Methyl 9(10)-hydroxy-10(9)-isopropoxystearate by Reaction of Epoxidized Rapeseed Oil Methyl Ester with Isopropanol 44.7 g (0.15 mol) of epoxidized rapeseed oil methyl ester were added to 56.3 g (0.94 mol) of isopropanol. Then, at room temperature, a total of 0.13 g (0.9 mmol) of $BF_3 \cdot OEt_2$ was slowly added dropwise, during which the reaction mixture warmed up to 50° C. Stirring was continued for 30 min without further heating, completeness of conversion was checked by GC analysis, and then 2 drops of $H_2O$ were added to hydrolyze the $BF_3 \cdot OEt_2$. The mixture was then concentrated under reduced pressure (45° C.). The resulting ester could be used directly for further reactions.

Example 26
Acid-Catalyzed Reaction of Epoxidized Rapeseed Oil Methyl Ester with Water 916.5 g (3.0 mol) of epoxidized rapeseed oil methyl ester were dissolved in 1200 ml of toluene and 108 g (6.0 mol) of water and 45.0 g (0.48 mol) of ortho-phosphoric acid (85% strength) were added. 13.0 g (20 mmol) of tetrabutylammonium hydroxide solution (40% strength) were added as phase-transfer catalyst. This mixture was refluxed for 4 h. Completeness of conversion was checked by epoxide titration, and then the mixture was concentrated under reduced pressure (50° C.). The resulting ester could be used directly for further reactions.

Example 27
Acid-Catalyzed Reaction of Epoxidized Soybean Oil with Water 124.5 g (0.5 mol) of epoxidized soybean oil were dissolved in 200 ml of toluene, and 18 g (1.0 mol) of water and 9.3 g (0.08 mol) of ortho-phosphoric acid (85% strength) were added. 3.1 g (5 mmol) of tetrabutylammonium hydroxide solution (40% strength) were added as phase-transfer catalyst. This mixture was refluxed for 5 h. Completeness of conversion was checked by epoxide titration, and the mixture was then concentrated under reduced pressure (45° C.). The resulting triglyceride could be used directly for further reactions.

Example 28
Reaction of Methyl Dihydroxystearate with Aminopropyldiethanolamine A mixture of 64.8 g (0.4 mol) of aminopropyldiethanolamine and 41.0 g of sodium methoxide solution (0.228 mol, 30% strength in methanol) was heated to 80° C. under a protective gas atmosphere and, at this temperature, 154.8 g (0.4 mol) of methyl dihydroxystearate from Example 26 were slowly added. The mixture was then heated to 100° C. and then stirred at this temperature for 1 h. Conversion was checked by GC and, after the reaction was complete, the product mixture was discharged. The reaction product was obtained as a highly viscous yellowish liquid.

Example 29
Reaction of Methyl 9(10)-hydroxy-10(9)-methoxystearate with Aminopropyldiethanolamine Methyl 9(10)-hydroxy-10(9)-methoxystearate from Example 24 was reacted with aminopropyldiethanolamine in the presence of sodium methoxide solution as in Example 28.

Use Properties

The use properties investigated for the fatty amide derivatives XXI were the interfacial tension, the contact angle, the surface tension, the cotton-wetting capacity, the solubility and the fat-removal capacity. The results of measurement of the substances of Examples 29 and 28 are summarized in Table 10.

The interfacial tension was determined as a function of the time of contact between aqueous surfactant solution and an oil phase.

The contact angle was measured as the wettability of a hard surface by the surfactant solution. In this case, complete wetting (spreading) corresponds to a contact angle of zero.

The surface tension was determined by the DIN 53914 method by measuring the force in mN/m necessary to pull a plate or a horizontally suspended ring out of the liquid surface.

To determine the fat-removal capacity, small solid plates covered with engine oil or neutral oil are immersed horizontally in the surfactant solution (c=1 g/l) to be investigated. The time until the first oil drop is removed from the particular plate is measured. A shorter time means a better fat-removal capacity.

TABLE 10

| Sample | Example 29 | | Example 28 | |
|---|---|---|---|---|
| Interfacial tension [mN/m] (1 g/l; 25° C.; 1 min) | | | | |
| Decane | 0.27 | | 1.0 | |
| Olive oil | 1.4 | | 0.11 | |
| Neutral oil | 0.24 | | 0.29 | |
| Pork fat 60° C. | 0.11 | | 0.13 | |
| Contact angle [degrees] (0.2 g/l; 40° C.) $H_2O$ | — | | — | |
| Polyethylene 110 | 0 | | 0 | |
| Stainless steel 76 | 0 | | 0 | |
| Ceramic 83 | 0 | | 0 | |
| Glass 77 | 30 | | 30 | |
| Surface tension [mN/m] | 0.2 g/l | 1 g/l | 0.2 g/l | 1 g/l |
| 25° C. | 29.6 | 30.4 | 32.1 | 31.6 |
| Cotton-wetting capacity [sec] | | 230 | | 280 |
| Solubility [1 g/l] (Turbidity units) Deionized water | | | | |
| 25° C. | 1 (clear) | | 1 (clear) | |
| 40° C. | 1 (clear) | | 1 (clear) | |

TABLE 10-continued

| Sample | Example 29 | Example 28 |
|---|---|---|
| Water of 20° hardness 25° C. Fat-removal capacity [sec] (1 g/l; 40° C.) (Olive oil) | 93 (slightly cloudy) | 780 (very cloudy) |
| Teflon | 117 | 3 |
| Polyethylene | 83 | 13 |
| Stainless steel | 88 | 4 |
| Ceramic | 68 | 4 |
| Glass | 56 | 5 |

The interfacial tensions of the reaction products according to the invention with respect to the various oils are in some cases distinctly lower than those of corresponding commercial saccharide surfactants and of corresponding fatty alcohol ethoxylates. The fat-removal capacity on various surfaces, especially for olive oil, of all the synthesized products is at least comparable with or distinctly better than with commercial surfactants. The reactions with aminopropyldiethanolamine in particular result in products with better colloid-chemical properties, especially with regard to the interfacial tension and the stability to water hardness.

The reaction product of Example 29 shows good biodegradability and elimination in the Zahn-Wellens test: the DOC elimination is <10% after 3 h and 60–70% after 28 d.

We claim:

1. A method of cleaning a grease-soiled nontextile material comprising contacting the material with a fatty acid derivative having formula I:

$$A^1\text{—CO—}R^1 \quad (I)$$

wherein $A^1$ is an aliphatic $C_8$–$C_{24}$ radical having an unbranched carbon chain which contains one or more groups represented by formula II:

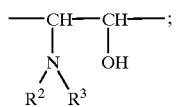

$R^1$ is, a hydroxyl radical or an alkali metal or ammonium salt thereof, a $C_1$–$C_4$-alkoxy radical, or a radical of a mono-, di- or triglyceride, it being possible for the two latter radicals to be of natural saturated or unsaturated fatty acids or identical or different radicals $A^1$;

$R^2$ is a hydrophilic radical having 2–40 carbon atoms; and $R^3$ is hydrogen, a $C_1$–$C_4$-alkyl radical or a hydrophilic radical having 2–40 carbon atoms.

2. The method as claimed in claim 1, wherein $A^1$ is derived from an unsaturated $C_{18}$ fatty acid.

3. The method as claimed in claim 1, wherein $R^2$ is an unbranched ω-hydroxyalkyl group or an unbranched ω-aminoalkyl group having 2 to 6 carbon atoms, it being possible for the alkyl radical to be interrupted by nonadjacent oxygen atoms, —NH groups, N-$C_1$–$C_4$-alkyl groups or N-$C_1$–$C_4$-hydroxyalkyl groups.

4. The method as claimed in claim 1, wherein $R^2$ is a polyalkylene glycol group having 3 to 40 carbon atoms.

5. The method as claimed in claim 1, wherein the nontextile material is a metal article.

6. The method as claimed in claim 1, wherein the nontextile material is contacted with an additional cleaning agent.

7. A method according to claim 1 wherein $R^1$ is a hydroxyl radical or an alkoxy radical.

8. A composition for cleaning nontextile materials, comprising water and a fatty acid derivative having formula I:

$$A^1\text{—CO—}R^1 \quad (I)$$

wherein $A^1$ is an aliphatic $C_8$–$C_{24}$ radical having an unbranched carbon chain which contains one or more groups represented by formula II:

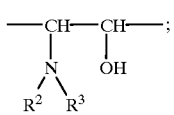

$R^1$ is a hydroxyl radical or an alkali metal or ammonium salt thereof, a $C_1$–$C_4$-alkoxy radical, or a radical of a mono-, di- or triglyceride, it being possible for the two later radicals to be of natural saturated or unsaturated fatty acids or identical or different radicals $A^1$;

$R^2$ is a hydrophilic radical having 2–40 carbon atoms; and $R^3$ is hydrogen, a $C_1$–$C_4$-alkyl radical or a hydrophilic radical having 2–40 carbon atoms.

9. A composition according to claim 8, where $R^1$ is a hydroxyl radical or an alkoxy radical.

* * * * *